United States Patent [19]
Levitzki et al.

[11] Patent Number: 5,990,277
[45] Date of Patent: Nov. 23, 1999

[54] SEMIPEPTOID FARNESYL PROTEIN TRANSFERASE INHIBITORS AND ANALOGS THEREOF

[75] Inventors: Alexander Levitzki; Chaim Gilon, both of Jerusalem; Hadas Reuveni, Aminadav, all of Israel

[73] Assignee: Yissum Research Development Company of the Herbrew University of Jerusalem, Jerusalem, Israel

[21] Appl. No.: 08/707,082

[22] Filed: Sep. 3, 1996

[51] Int. Cl.[6] ................................................... A61K 38/07
[52] U.S. Cl. ........................................... 530/330; 530/331
[58] Field of Search ................ 514/18, 19; 530/330–331

[56] References Cited

U.S. PATENT DOCUMENTS

| | | | |
|---|---|---|---|
| 5,585,359 | 12/1996 | Breslin et al. | 514/19 |
| 5,705,686 | 1/1998 | Sebti et al. | 562/557 |

FOREIGN PATENT DOCUMENTS

| | | |
|---|---|---|
| 0 444 898A1 | 2/1991 | European Pat. Off. |
| 0 461869 A2 | 12/1991 | European Pat. Off. |
| WO 91/19735 | 6/1991 | WIPO |

OTHER PUBLICATIONS

Clerc, F. Et al, "Constrained Analogs Of KCVFM With Improved Inhibitopry Properties Against Farnesyl Transferase", *Bioorganic & Medicinal Chem. Ltrs.*, vol. 5, No. 16, pp. 1779–1784 (1995).

Leftheris, K. Et al, "Peptide Based $p21^{ras}$ Farnesyl Transferase Inhibitors: Systematic Modification of the Tetrapeptide $CA_1A_2X$ Motif", *Bioorganic & Medicinal Chem. Ltrs.*, vol. 4, pp. 887–892 (1994).

Patel, D.V. et al, "Phosphinyl Acid–Based Bisubstrate Analop Inhibitors of Ras Farnesyl Protein Transferase", *J. Med. Chem.*, vol. 38, No. 3, pp. 435–442 (1995).

Williams, T.M. et al, "2–Substituted Piperazines as Constrained Amino Acids, Application to the Synthesis of Potent, Non Carboxylic Acid Inhibitors of Farnesyltransferase", *J. Med. Chem.*, vol. 39, No. 7, pp. 1345–1348 (1996).

Lerner, E. et al, "Disruption of Oncogenic K–Ras4B Processing and Signalling by a Potent Geranylgeranyltransferase I Inhibitor", *J. Biol. Chem.*, vol. 270, No. 45, pp. 26770–26773 (1995).

Cox, A.D. et al, "The CAAX Peptidomimetic Compound B581 Specifically Blocks Farnesylated, But Not Geranylgeranylated or Myristylated, Oncogenic Ras Signaling and Transformation", *J. Biol. Chem.*, vol. 269, No. 30, pp. 19203–10206 (1994).

Graham, S.L. et al. "Pseudopeptide Inhibitors of Ras Farnesyl–Protein Transferase", *J. Med Chem.*, vol. 37, No. 6, pp. 725–732 (1994).

Kohl, N.E. et al, "Selective Inhibition of ras–Dependent Transformation by a Farnesyltransferase Inhibitor" *Science*, Vil. 260, pp. 1934–1936 (Jun. 1993).

James, G.L. et al, "Benzodiazepine Peptidomimetics: Potent Inhibitors of Ras Farneslation in Animal Cells", *Science*, vol. 260, pp. 1937–1942 (Jun. 1993).

Hancock, J.F., "Anti–Ras Drugs Come of Age", *Current Biology*, vol.3, No. 11, pp. 770–772 (1993).

Gibbs, J.B. et al, "Farnesyltransferase Inhibitors: Ras Research Yields a Potential Cancer Therapeutic", *Cell* vol. 77, pp. 175–178 (Apr. 1994).

Manne, V. Et al, "Bisubstrate Inhibitors of Farnesyltransferase: A Novel Class of Specific Inhibitors of Ras Transformed Cells", *Oncogene*, vol. 10, pp. 1763–1779 (1995).

Vogt, A. Et al, "A Non–Peptide Mimetic of Ras–CAAX: Selective Inhibition of Farnesyltransferase and Ras Processing", *J. Biol. Chem.*, vol. 270, No. 2, pp. 660–664 (1995).

Byk, G. Et al, "Local Constrained Shifty Pseudopeptides Inhibitors of Ras–Farnesyl Transferase" Bioorganic & Medical Letters, vol. 5, No. 22, pp. 2677–2682 (1995).

Kohl, N.E. et al, "Inhibition of Farnesyltransferase Induces Regression of Mammary and Salivary Carcinomas in ras Transgenic Mice", *Nature Medicine*, vol. 1, No. 8, pp. 792–797 (1995).

Kohl, N.E. et al, "Protein Farnesyltransferase Inhibitors Block the Growth of ras–Dependent Tumors in Nude Mice", *Proc. Nat. Acad. Sci. USA*, vol. 91 pp. 9141–9145 (1994).

Leftheris, K. Et al, "Development of Highly Potent Inhibitors of Ras Farnesyltransferase Possessing Cellular and in vitro Activity", *J. Med Chem.*, vol. 39, pp. 224–236 (1996).

Brown, M. S. Et al, "Tetrapeptide Inhibitors of Protein Farnesyltransferase: Amino–Terminal Substitution in Phenylalanine–Containing Tetrapeptides Restores Farnesylation", *Proc. Nat. Acad. Sci. USA*, vol. 89, pp. 8313–8316 (1992).

Kato, K. Et al, "Isoprenoid Addition to Ras Protein is the Critical Modification for its Membrane Association and Transforming Activity", *Proc. Nat. Acad. Sci. USA*, vol. 89, pp. 6403–6407 (1992).

Hancock, J.F. et al, "All ras Proteins are Polyisoprenylated But only Some aare Palmitoylated", *Cell*, vol. 57, pp. 1167–1177 (1989).

Goldstein, J.L. et al, "Nonfarnesylated Tetrapeptide Inhibitors of Protein Farnesyltransferase", *J. Biol. Chem.*, vol. 266, No. 24, pp. 15575–15578 (1991).

Zuckermann, R.N. et al, "Efficient Method for the Preparation of Peptoids [Oligo (N–substituted glycines)] by Submonomer Solid–Phase Synthesis", *J. Am. Chem. Soc.*, vol. 114, pp. 10646–10647 ((1992).

(List continued on next page.)

*Primary Examiner*—Bennett Celsa
*Attorney, Agent, or Firm*—Mark M. Friedman

[57] ABSTRACT

A farnesyl protein transferase (i.e., farnesyltransferase) inhibitors formed as peptoid and semipeptoid peptidomimetic compounds derived from a farnesyltransferase universal recognition tetrapeptide sequence CAAX (i.e., CAAX motif) and analogs thereof, and to the use of these compounds and analogs and ester derivatives thereof as chemotherapeutic agents in oncogenic or non-oncogenic Ras associated cancers and proliferative diseases.

10 Claims, 4 Drawing Sheets

OTHER PUBLICATIONS

Zuckermann, R.N. et al, "Discovery of Nanomolar Ligands for 7—Transmembrane G–Protein–Coupled Receptors from a Diverse N–(Substituted) Glycine Peptoid Library", *J. Med. Chem.*, vol. 37, pp. 2678–2685 (1994).

Kessler, H., "Peptides –A New Approach to the Development of Pharmaceuticals", *Angew. Chem. Int. Ed. Engl.*, vol. 32, No. 4, pp. 543–544 (1993).

Simon, R.J. et al, "Peptoids: A Modular Approach to Drug Discovery", *Proc. Nat. Acad. Sci. USA*, vol. 89, pp. 9367–9371 (1992).

Miller, S.M. et al, "Comparison of the Proteolytic Susceptibilities of Homologous L–Amino Acid, and N–Substituted Glycine Peptide and Peptide Oligomers", *Drug Development Research*, vol. 35, No. 20, pp. 20–32 (1995).

Moores, S.L. et al, "Sequence dependence of Protein Isoprenylation", *J. Biol. Chem.*, vol. 266, No. 22, pp. 14603–14610, (1991).

Miller, S.M. et al, "Proteolytic Studies of Homologous Peptide and N–Substituted Glycine Peptide and Peptide Oligomers", *Bioorg. & Med. Chem. Ltrs.*, vol. 4, No. 22, pp. 2657–2662 (1994).

Gallop, M.A. et al, "Applications of Combinatorial Technologies to Drug Discovery. 1. Background and Peptide Combinatorial Libraries", *J. Med. Chem.*, vol. 37, No. 9, pp. 1233–1251 (1994).

Gibbs, J.B., "Ras C–Terminus Processing Enzymes——New Drug Targets?" *Cell*, vol. 65, pp. 1–4 (1991).

Reiss, Y. et al, "Sequence requirement for Peptide Recognition by Rat Brain p21$^{ras}$ Protein Farnesyltransferase", *Proc. Natl. Acad. Sci. USA*, vol. 88, pp. 732–736 (1991).

Houghten, R.A., "General Method for the Rapid Solid–Phase Synthesis of Large Numbers of Peptides: Specificity of Antigen–Antibody Interaction at the Level of Individual Amino Acids", *Proc. Natl. Acad. Sci. USA*, vol. 82, pp. 5131–5135 (1985).

deSolms, S. J. et al, "Pseudopeptide Inhibitors of Protein Farneslytransferase", *J. Med. Chem.*, vol. 38, pp. 3967–3971 (1995).

Garcia, A.M. et al, "Peptidomimetic Inhibitors of Ras Farnesylation and Function in Whole Cells", *J. Biol. Chem.*, vol. 268, No. 25, pp. 18415–18418 (1993).

Reiss, Y. Et al, "Inhibition of Purified p21$^{ras}$ Farnesyl: Protein Transferase by Cys–AAX Tetrapeptides", *Cell*, vol. 62, pp. 81–88, (1990).

Kruijtzer, J.A. et al, "Synthesis in Solution of Peptoids using Fmoc–Protected N–Substituted Glycines", *Tetrahedron Letters*, vol. 36, No. 38, pp. 6969–6972 (1995).

Bodor, N. et al, "A Strategy for Delivering Peptides into the Central Nervous System by Sequential Metabolism", *Science*, vo. 257, pp. 1698–1700 (1992).

Maltese, W.A., "Posttranslational Modification of Proteins by Isoprenoids in Mammalian Cells", *FASEB Journal*, vol. 4, pp. 3319–3328, (1990).

SEMIPEPTOID FARNESYL PROTEIN TRANSFERASE INHIBITORS AND ANALOGS THEREOF

FIELD AND BACKGROUND OF THE INVENTION

The present invention relates in general to farnesyl protein transferase (i.e., farnesyltransferase) inhibitors. More particularly, the present invention relates to peptoid and semipeptoid peptidomimetic compounds derived from a farnesyltransferase universal recognition tetrapeptide sequence CAAX (i.e., CAAX motif, SEQ ID NO:1) and analogs thereof, and to the use of these compounds and analogs and ester derivatives thereof as chemotherapeutic agents in oncogenic as well as non-oncogenic Ras associated cancers and other proliferative diseases.

The use of peptides as drugs is limited by the following factors: (a) their low metabolic stability towards proteolysis in the gastrointestinal tract and in serum; (b) their poor absorption after oral ingestion, in particular due to their relatively high molecular mass or the lack of specific transport systems or both; (c) their rapid excretion through the liver and kidneys; (d) their undesired side effects in non-target organ systems, since peptide receptors can be widely spread in an organism; and (e) their high immunogenicity.

In recent years intensive effort has been directed towards the development of peptidomimetics (i.e., peptide analogs) that display more favorable pharmacological properties than their peptide prototypes. A peptidomimetic is a compound that, as a ligand of a receptor, can imitate or block the activity and biological effect of a peptide at the receptor level (Giannis and Kotler, Angew. Chem. Int. Ed. Engl., 1993, 32: 1244). The following requirements exist for the pharmacological properties of a peptidomimetic: (a) metabolic stability; (b) good bioavailability; (c) high receptor affinity and receptor selectivity; and (d) minimal side effects.

The native peptide itself, the pharmacological properties of which should be optimized, generally serves as the lead structure for the development of peptidomimetics. With few exceptions, linear peptides of small or medium size (<30–50 amino acid units) exist in dilute aqueous solution in a multitude of conformations in dynamic equilibrium. If a receptor ligand has a biological active conformation per se, in other words, the receptor-bound conformation, then an increased affinity toward the receptors is expected and generally experienced, as compared with the flexible ligand.

From a pharmacological and medical points of view, it is in many cases desirable not only to imitate the effect of the peptide at the receptor level, as an agonist, but also to block the receptor, as an antagonist. The same pharmacological considerations mentioned above holds for peptide antagonists, but, in addition, their development in the absence of lead structures is more difficult. In most cases it is not unequivocally clear which factors are decisive for an agonistic effect and which are for antagonistic effect.

A generally applicable and successful method for the development of peptidomimetics involves formation of conformationally restricted analogs that imitate the receptor-bound conformation of the endogenous ligands as closely as possible (see, Rizo and Gierasch, Ann. Rev. Biochem., 1992, 61: 387). Investigating these analogs demonstrated their increased resistance toward proteases resulting in increased metabolic stability, as well as their increased selectivity. As a result of these properties, peptidomimetics produce less side effects (Veber and Friedinger, Trends Neurosci., 1985, 8: 392–396). The observation that in many cases only a small number (e.g., four to eight) of amino acid side chains of a peptidic ligand are responsible for recognition of the ligand by its receptor turns out to be favorable for this approach. In such cases the rest of the ligand molecule framework serves to fix the amino acids responsible for recognition, also known in the art as pharmacophores, in a specific spatial arrangement.

Compounds having a rigid conformation are then produced, and the most active structures are selected by assays analyzing the structure-activity relationship. Such conformational constraints can involve short range (local) modifications of the structure or long range (global) conformational restraints.

For example, bridging between two neighboring amino acids in a peptide leads to local conformational modifications, the flexibility of which is limited in comparison with that of a native dipeptides. Some possibilities for forming such bridges include incorporation of lactams and piperazinones. γ-lactams and δ-lactams have been designed as "turn-mimetics"; in several cases the incorporation of such structures into peptides lead to biologically active compounds (Giannis and Kotler, Angew. Chem. Int. Ed. Engl., 1993, 32: 1244).

Global restrictions on the conformation of a peptide are possible by limiting the flexibility of the peptide strand through cyclization (Hruby el al., Biochem. J., 1990, 268: 249). For this purpose, amino acid side chains that are not involved in receptor recognition are bridged together or to the peptide backbone. Three representative examples are compounds wherein partial structures of each peptide are made into rings by linking two pennicillamine residues with a disulfide bridge (Mosberg et al., Proc. Natl. Acad. Sci. USA, 1983, 80: 5871), by formation of an amide bond between a lysine and an aspartate group (Charpentier et al., J. Med. Chem., 1989, 32: 1184), or by connecting two lysine groups with a succinate unit (Rodriguez et al., Int. J. Pept. Protein Res., 1990, 35: 441). These structures have been disclosed in the literature in the case of a cyclic enkephalin analog with selectivity for the δ opiate receptor (Mosberg et al., Proc. Natl. Acad. Sci. USA, 1983, 80:5871); or as agonists to the cholecystokinin-B receptor, found largely in the brain (Charpentier et al., J. Med. Chem., 1989, 32: 1184, Rodriguez et al., Int. J. Pept. Protein Res., 1990, 35: 441).

Another conceptual approach to the conformational constraint of peptides was introduced by Gilon et al. (Biopolymers, 1991, 31: 745) who proposed backbone to backbone cyclization of peptides. The theoretical advantages of this strategy include the ability to effect cyclization via the carbon or the nitrogen of the peptide backbone without interfering with side chains that may be crucial for interaction with a specific receptor of a given peptide. While the concept was envisaged as being applicable to any linear peptide of interest, in fact the limiting factor in the proposed scheme was the availability of suitable building units that must be used to replace the amino acids that are to be linked via bridging groups. The actual reduction to practice of the backbone cyclization concept was prevented by the inability to device a practical method of preparing suitable building units of amino acids other than glycine (Gilon et al., J. Org. Chem., 1992, 57: 5687). While analogs of other amino acids were attempted, the synthetic method used was unsuccessful or of a low yield as to preclude any general applicability.

Gilon et al. describe two basic approaches for the synthesis of suitable building units to produce building units for Boc and Fmoc chemistry peptide synthesis. For further details see, EP 564739A2 October, 1993; and Gilon et al. J.

Org. Chem., 1992, 57: 5687). Both approaches deal with the reaction of a molecule of the general type X—CH(R)—CO—OR' (where X represents a leaving group which, in the example given, is either Br or Cl) with an amine which replaces the leaving group X. The amine bears the alkylidene chain which is terminated by another functional group, amine in the example described, which may or may not be blocked by a protecting group. In all cases the α nitrogen of the end product originates in a molecule which becomes the bridging chain for subsequent cyclization. This approach was chosen in order to take advantage of the higher susceptibility to nucleophilic displacement of a leaving group located next to the carboxylic group.

Peptoids are polimeric compounds formed by shifting amino acid side chains from the Cα to the backbone nitrogen atom to yield Nα-alkylated oligoglycine derivatives (Simon et al.,. Proc. Natl. Acad. Sci. USA, 1992, 89: 9367, WO 91/19735 (June, 1991) by Bartlett). Semipeptoids are polimeric compounds containing both Nα-alkylated glycine derivatives and natural amino acids wherein the side chains are at Cα. As referred herein in this document and especially in the claims section below, peptoid and semipeptoid analogs refer to chemical modifications such as but not limited to alkylation, hydroxylation dealkylation or dehydroxylation of one or more side chains at Cα or Nα of the peptoid or semipeptoid backbone. For further details regarding peptoids, semipeptoids and their chemistry the reader is referred to WO 91/19735 by Bartlett.

An important therapeutic advantage of peptoids as compared to peptides is their resistance to proteases (Miller et al., Med. Chem. Lett., 1994, 4: 2657; Miller et al., Drug Development Research, 1995, 35: 20). In addition, the peptoids approach permits sophisticated structure-function relationship studies using both natural (i.e., native, conventional) and unnatural (i.e., analog) side chains by simple chemistry. A few peptoids were already found to be biologically active (Simon et al., Proc. Natl. Acad. Sci. USA, 1992, 89: 9367; Zuckermann et al., J. Med. Chem., 1994, 37: 2678; Kessler, Angew. Chem. Int. Ed. Engl., 1993, 32: 543).

Oncogenic Ras is found in 40% of all cancers and is involved in over 90% of pancreatic tumors and over 50% of colon carcinomas (Gibbs et al., Cell, 1994, 77: 175). Thus, inhibition of the Ras function is believed to be a crucial target for cancer chemotherapy (Gibbs, Cell, 1991, 65: 1). Membrane localization of the oncogenic Ras is critical for its function and transformative potential (Kato et al., Proc. Natl. Acad. Sci. USA, 1992, 89: 6403). This membrane binding is achieved through a series of post translational modifications directed by its carboxy-terminal CAAX motive (SEQ ID NO:1) (where C is cysteine, A is an aliphatic residue and X is preferably serine or methionine). The first and most essential modification is farnesylation of the conserved cysteine residue, catalyzed by the enzyme farnesyltransferase. Subsequent modifications are dependent on its previous occurrence (Hancock, Current biology 1993, 3: 770). Inhibition of the farnesylation reaction either by site directed mutagenesis (Hancock et al., Cell, 1989, 57: 1167) or by synthetic farnesyltransferase inhibitors nullifies Ras membrane anchorage and reverses transformation by oncogenic Ras (Gibbs et al., Cell, 1994, 77: 175). Recent findings show that inhibition of farnesyltransferase by various CAAX (SEQ ID NO:1) peptidomimetics cause regression of ras-induced transformation is in whole cells (Cox et al., J. Biol. Chem., 1994, 269: 19203; Manne et al., Oncogene, 1995, 10: 1763; Patel et al., J. Med. Chem., 1995, 38: 435; Kohl et al., Science, 1993, 260: 1934; James et al., Science, 1993, 260: 1937) and in animals without significant toxic effects (Kohl et al., Proc. Natl. Acad. Sci. USA, 1994, 91: 9141; Kohl et al., Nature Medicine, 1995, 1: 792).

For example, the peptidomimetic compound L-739,749 (2(S)-[2(CH(CH$_3$)$_2$)-amino-3-mercapto]-propylamino-3(S)-methyl]pentyloxy-3 phenylpropionyl methionine sulphone methyl ester, SEQ ID NO:2) is a farnesyl protein transferase inhibitor. This compound (Kohl et al., Proc. Natl. Acad. Sci. USA, 1994, 91: 9141) selectively blocks ras-dependent transformation of cells in culture, by suppressing the anchorage-independent growth of RatI cells transformed with viral H-ras. Compound L-739,749 described therein was also found to inhibit the anchorage-independent growth of human adenocarcinoma cell line PSN-1, which harbors altered K-ras and p53 genes, and to suppress the growth of tumors in nude mice.

Another compound, designed by Kohl et al. as L-744,832 (2(S)-[2(CH(CH$_3$)$_2$)-amino-3-mercapto]-propylamino-3(S)-methyl]pentyloxy-3-phenylpropionyl methionine sulphone isopropyl ester, SEQ ID NO:3) is the isopropyl ester derivative of compound L-739,750 (2(S)-[2(CH(CH$_3$)$_2$)-amino-3-mercapto]-propylamino-3(S) methyl]pentyloxy-3-phenylpropionyl methionine sulphone, SEQ ID NO:4), mimics the CAAX motif (SEQ ID NO:1) to which the farnesyl group is added during the post-translational modification process of Ras oncoprotein was found to be a potent and selective inhibitor of farnesyltransferase. In MMTV-v-Ha-ras transgenic mice bearing palpable tumors (Kohl et al., Nature Medicine, 1995, 1: 792), daily administration of compound L-744,832 caused tumor regression. These results suggest that, in some cancers, CAAX (SEQ ID NO:1) analog farnesyltransferase inhibitors may be used as anti tumor agents (Gibbs et al., Cell, 1994, 77: 175).

SUMMARY OF THE INVENTION

According to the present invention there are provided farnesyl protein transferase (i.e., farnesyltransferase) inhibitors in the form of peptoid and semipeptoid peptidomimetic compounds derived from a farnesyltransferase universal recognition tetrapeptide sequence CAAX (i.e., CAAX motif, SEQ ID NO:1) and analogs thereof, and to a chemotherapeutic treatment using these compounds and analogs and ester derivatives thereof as chemotherapeutic agents in oncogenic or non-oncogenic Ras associated cancers and proliferative diseases.

According to further features in preferred embodiments of the invention described below, the compound comprising a semipeptoid analog of farnesyl protein transferase recognition tetrapeptide sequence motif CA$_1$A$_2$X (SEQ ID NO:1).

According to still further features in the described preferred embodiments the compound further comprising at least one backbone chemical modification.

According to still further features in the described preferred embodiments the at least one backbone chemical modification is selected from the group consisting of Nα-alkylation, Cα-alkylation.

According to still further features in the described preferred embodiments the Nα-alkylation and Cα-alkylation are each selected from the group consisting of methylation, haloalkylation, alkenylation, cycloalkylation, alkoxyalkylation, arylalkylation, aminoalkylation, carboxyalkylation, carboalkoxyalkylation, carbamylation, carbamylalkylation, guanidinolation, guanidinoalkylation, mercaptolation, mercaptoalkylation, alkylthiolation, alkylthioalkylation, imidazolylation, imidazolalkylation, pyridylation, pyridylalkylation, piperidylation, piperidylalkylation, indolylation and indolyalkylation.

According to still further features in the described preferred embodiments the semipeptoid analog includes side chains selected from the group consisting of native amino acid side chains and chemically modified amino acid side chains.

According to still further features in the described preferred embodiments the semipeptoid analog includes side chains selected from the group consisting of alkyl moieties and aryl moieties.

According to still further features in the described preferred embodiments the alkyl and aryl moieties are selected from the group consisting of t-butyl, cyclohexyl, cyclohexyl derivatives, phenyl, phenyl derivatives, benzyl, benzyl derivatives, naphtyl, and naphtyl derivatives.

According to still further features in the described preferred embodiments the native and chemically modified side chains are selected from the group consisting of: (a) sulfhydryl for the C; (b) isopropyl, N,N-dimethylaminoethyl and isobutyl for the $A_1$; (c) benzyl, phenethyl, 3,4-dimetoxyphenethyl and cyclohexyl for the $A_2$; and (d) hydroxyl and methyl for the X.

According to still further features in the described preferred embodiments the compound is cysteinyl-valyl-(Nα-benzyl)glycyl-methionine (SEQ ID NO:5), cysteinyl-valyl-(Nα-phenethyl)glycyl-methionine (SEQ ID NO:6), cysteinyl-valyl-(Nα-3,4-dimetoxyphenethyl)glycyl-methionine (SEQ ID NO:7), cysteinyl-valyl-(Nα-cyclohexyl)glycyl-methionine (SEQ ID NO:8), cysteinyl-(Nα-isopropyl)glycyl-(Nα-benzyl)glycyl-methionine (SEQ ID NO:9), cysteinyl-(Nα-isopropyl)glycyl-(Nα-3,4-dimetoxyphenethyl)glycyl-methionine (SEQ ID NO:10), cysteinyl-(Nα(N,N-dimethylaminoethyl))glycyl-(Nα-benzyl)glycyl-methionine (SEQ ID NO:11), cysteinyl-(Nα-isopropyl)glycyl-phenylalanyl-methionine (SEQ ID NO:12), cysteinyl-(Nα(N,N-dimethylaminoethyl))glycyl-phenylalanyl-methionine (SEQ ID NO:13), cysteinyl-(Nα-isobutyl)glycyl-phenylalanyl-methionine (SEQ ID NO:14) or cysteinyl-(Nα-methyl)valyl-(Nα-cyclohexyl)glycyl-methionine (SEQ ID NO:15).

According to still further features in the described preferred embodiments the compound comprising a chemical of the general formula $C-A_1(R_1)-A_2(R_2)-X$ (SEQ ID NO:1), wherein (a) the C is selected from the group consisting of cysteinyl and N-substituted-glycine analog of cysteinyl; (b) the $A_1(R_1)$ is selected from the group consisting of a first aliphatic amino-acid residue and N-substituted-glycine peptoid analog of the first aliphatic amino-acid residue, the $R_1$ is selected from the group consisting of a native first side chain of the first aliphatic amino-acid residue and a chemical modification of the native first side chain; (c) the $A_2(R_2)$ is selected from the group consisting of a second aliphatic amino-acid residue and N-substituted-glycine peptoid analog of the second aliphatic amino-acid residue, the $R_2$ being selected from the group consisting of a native second side chain of the second aliphatic amino-acid residue and a chemical modification of the native second side chain; (d) the X is selected from the group consisting of methionine, serine, R substituted ethionine, N-substituted-glycine peptoid analog of methionine, N-substituted-glycine peptoid analog of methionine, N-substituted-glycine peptoid analog of R substituted ethionine sulfoxide methionine, sulfoxide serine, sulfoxide R substituted ethionine, sulfoxide N-substituted-glycine peptoid analog of methionine, sulfoxide N-substituted-glycine peptoid analog of methionine, sulfoxide N-substituted-glycine peptoid analog of R substituted ethionine, sulfone methionine, sulfone serine, sulfone R substituted ethionine, sulfone N-sub stituted-glycine peptoid analog of methionine, sulfone N-substituted-glycine peptoid analog of methionine and sulfone N-substituted-glycine peptoid analog of R substituted ethionine; and (e) the compound includes at least one N-substituted-glycine analog.

According to still further features in the described preferred embodiments the first and second aliphatic amino-acid residues are selected from the group of aliphatic amino acid residues consisting of valyl, phenylalanyl, alanyl leucinyl and isoleucinyl, and the N-substituted-glycine peptoid analogs of the first and second aliphatic amino-acid residues are selected from the group consisting of (Nα-isopropyl) glycyl and (Nα-phenethyl)glycyl.

According to still further features in the described preferred embodiments the native first and second side chains of the first and second aliphatic amino-acid residues are selected from the group consisting of isopropyl and phenethyl, and the chemical modification of the native first and second side chains are selected from the group consisting of N,N-dimnethylaminoethyl, isobutyl, benzyl, 3,4-dimetoxyphenethyl and cyclohexyl.

According to still further features in the described preferred embodiments the compound comprising a chemical of the general formula $C-A_1-A_2-X$ (SEQ ID NO:1), wherein (a) the C is selected from the group consisting of cysteinyl and N-substituted-glycine analog of cysteinyl; (b) the $A_1$ is selected from the group consisting of a first C-alkyl-substituted-glycine, a first C-aryl-substituted-glycine, a first N-alkyl-substituted-glycine and a first N-aryl-substituted-glycine; (c) the $A_2$ is selected from the group consisting of a second C-alkyl-substituted-glycine, a second C-aryl-substituted-glycine, a second N-alkyl-substituted-glycine and a second N-aryl-substituted-glycine; (d) the X is selected from the group consisting of methionine, serine, N-substituted-glycine analog of methionine and N-substituted-glycine analog of methionine; and (e) the compound includes at least one N-substituted-glycine.

According to still further features in the described preferred embodiments the first and second C-alkyl-substituted-glycine are each selected from the group consisting of valyl, (Cα-isopropyl)glycyl, (Cα(N,N-dimethylaminoethyl)) glycyl and (Cα-isobutyl)glycyl.

According to still further features in the described preferred embodiments the first and second N-alkyl-substituted-glycine are each selected from the group consisting of valyl, (Nα-isopropyl)glycyl, (Nα(N,N-dimethylaniinoethyl))glycyl and (Nα-isobutyl)glycyl.

According to still further features in the described preferred embodiments the first and second C-aryl-substituted-glycine are each selected from the group consisting of phenylalanyl, (Cα-benzyl)glycyl, (Cα-3,4-dimetoxyphenethyl)glycyl and (Cα-cyclohexyl)glycyl.

According to still further features in the described preferred embodiments the first and second N-aryl-substituted-glycine are each selected from the group consisting of phenylalanyl, (Nα-benzyl)glycyl, (Nα-3,4-dimetoxyphenetlyl)glycyl and (Nα-cyclohexyl)glycyl.

According to still further features in the described preferred embodiments any of the compounds further comprising a C-terminus hydrophobic moiety.

According to still further features in the described preferred embodiments the hydrophobic moiety is an ester moiety and is selected from the group consisting of alkyl ester and aryl ester.

According to still further features in the described preferred embodiments the alkyl and aryl esters are selected from the group consisting of methyl ester, ethyl ester, hydroxyethyl ester, t-butyl ester, cholesteryl ester, isopropyl ester and glyceryl ester.

According to still further features in the described preferred embodiments the chemotherapeutic treatment comprising administration of any of the compound to a living creature such as a human.

According to still further features in the described preferred embodiments the treatment is for inhibition of farnesyl protein transferase in oncogenic or non-oncogenic Ras associated cancers and proliferative diseases.

It is one object of the present invention to provide a farnesyl protein transferase (i.e., farnesyltransferase) inhibitors in the form of peptoid and semipeptoid peptidomimetic compounds derived from a farnesyltransferase universal recognition tetrapeptide sequence CAAX (i.e., CAAX motif, SEQ ID NO:1).

It is another object of the present invention to provide analogs of the peptoid and semipeptoid peptidomimetic compounds, which analogs act better in farnesyl protein transferase inhibition.

It is another object of the present invention to provide a chemotherapeutic treatment using these compounds and analogs and ester derivatives thereof as chemotherapeutic agents in oncogenic or non-oncogenic Ras associated cancers and proliferative diseases.

BRIEF DESCRIPTION OF THE DRAWINGS

The invention herein described, by way of example only, with reference to the accompanying drawings, wherein.

DESCRIPTION OF THE PREFERRED EMBODIMENTS

Figure 1:
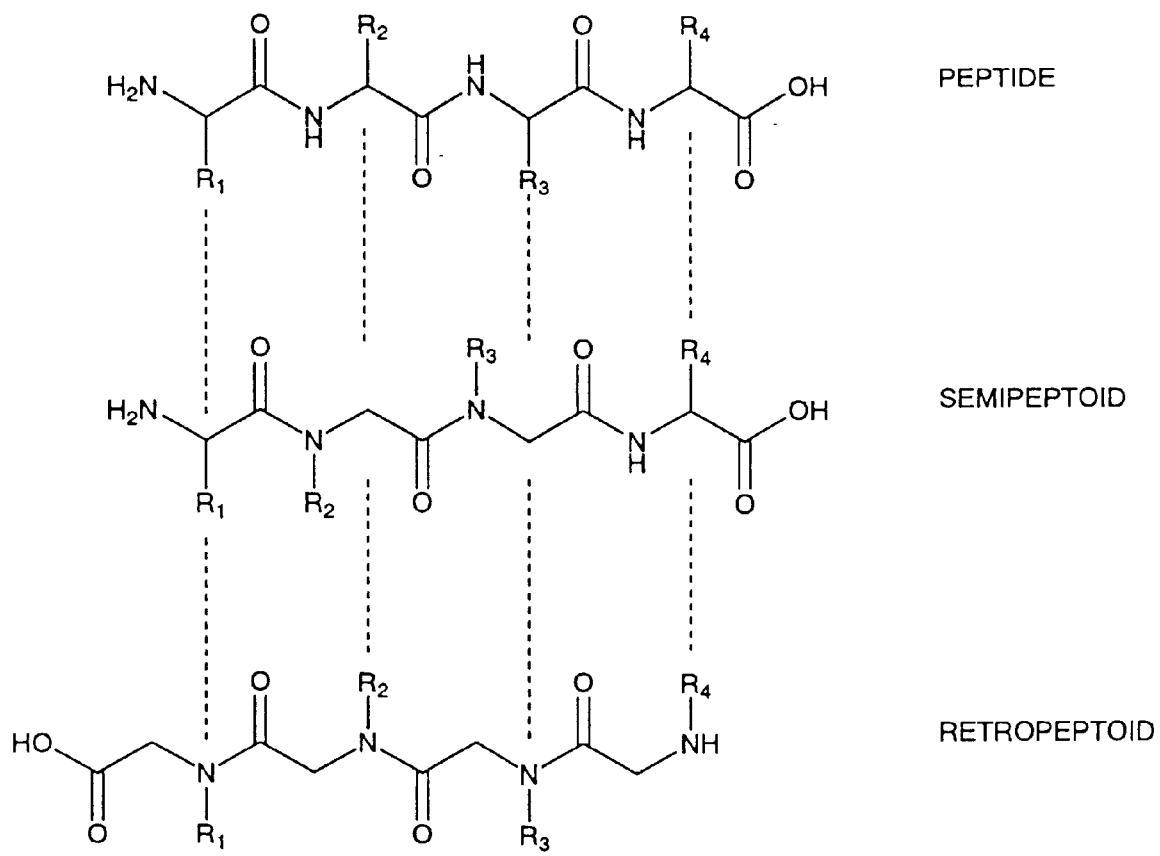
FIG. 1 is a schematic depiction of the topological relation of a tetrapeptide, its semipeptoid and its retropeptoid analogs. The relation of the side chains are shown in doted line.

The present invention is of peptoid and semipeptoid peptidomimetic compounds derived from a farnesyltransferase universal recognition (i.e., motif) tetrapeptide sequence CAAX (SEQ ID NO:1) and analogs thereof which can be used after esterefication or other hydrophobication process as chemotherapeutic agents in oncogenic or non-oncogenic Ras associated cancers and proliferative diseases.

Definitions

Throughout this document, abbreviations of amino acids are according to the IUPAC-FUB commission on biochemical nomenclature (1975).

| Abbreviated Designation | Compounds |
| --- | --- |
| FT | Farnesyltransferase |
| GGT | Geranylgeranyltransferase |
| NSG | N-substituted glycine |
| MAPS | Multiple analog peptide synthesis |
| Fmoc | Fluoren-9-ylmethoxycarbonyl |
| Boc | tert-Butyloxycarbonyl |
| Trt | Trityl(Triphenylmethyl) |
| DIC | N,N'-diisopropyl carbodiimide |
| PyBroP | Bromo-tris-pyrrolidino-phosphonium hexafluorophosphate |
| BOP | enzotriazolyl-N-oxy-tris(dimethylamnino) phosplionium hexafluorophosphate |
| DIEA | Diisopropylethylamine |
| DMSO | Dimethylsulfoxide |
| DMF | Dimethylformamide |
| TFA | Trifluoroacetic acid |
| TCA | Trichloroacetic acid |
| DTT | 1,4-dithiothreitol |
| SDS | Sodium dodecyl sulfate |
| Gst | Glutathione-S-transferase |
| RP | Reverse phase |
| FAB-MS | Fast atom bombardment mass spectroscopy |
| TOF-MS | Time of flight mass spectroscopy |

Chemical Synthesis

It has been previously shown that for FT inhibitors based on the $CA_1A_2X$ structure, the cysteine is essential for improved potency of the inhibitor (Goldstein et al., J. Biol. Chem., 1991, 266: 15575; Reiss et al., Proc. Natl. Acad. Sci. USA, 1991, 88: 732; and, Brown et al., Proc. Natl. Acad. Sci. USA, 1992, 89: 8313). A methionine at the X position is required for both potency and selectivity (Reiss et al., Proc. Natl. Acad. Sci. USA, 1991, 88: 732; Moores et al., J. Biol. Chem., 1991, 266: 14603), while the $A_1A_2$-spacer may tolerate certain modifications (James et al., Science, 1993, 260: 1937; Goldstein et al., J. Biol. Chem., 1991, 266: 15575; Nigam et al., J. Biol. Chem., 1993, 268: 20695; Qian et al., J. Biol. Chem., 1994, 269: 12410).

Thus, for screening of potent and specific FT inhibitors the N-terminal cysteine and the C-terminal methionine were conserved and an N-substituted-glycine (NSG) units were built at positions $A_1$ and/or $A_2$ to obtain CAAX (SEQ ID NO:1) semipeptoids which are potent and specific FT inhibitors both in vitro and in vivo.

The goals of the modifications are (i) to increase the metabolic stability and cell permeability of the parent peptide (ii) to examine whether shifting the side chains of the $A_1/A_2$ residues would influence the potency and selectivity towards FT (iii) to determine if shifting the $A_1A_2$ side chains is permissible by performing structure activity relationship studies on these side chains.

For this purpose a library of ten semipeptoids was constructed by the "tea bags" multiple analog peptide synthesis (MAPS) method, first developed by Houghten (Houghten, Proc. Natl. Acad. Sci. USA, 1985, 82: 5131; Gallop et al., J. Med. Chem., 1994, 37: 1233, incorporated by reference as if fully set forth herein).

As shown in Table I below, the library was divided into three classes. In class I (semipeptoids 1–4, Table I) a valine residue is conserved at position $A_1$ while the phenylalanine at the $A_2$ position is replaced by NSG with different substituents on the amine. In class II (semipeptoids 5–7, Table I) both $A_1$ and $A_2$ residues are replaced by NSG units. While the substituents at the $A_2$ position were mainly aromatic, those at the $A_1$ position were aliphatic, as in the original CVFM (SEQ ID NO:16) peptide inhibitor. In class III (semipeptoids 8–10, Table I), the phenylalanine was untouched and only the $A_1$ residue was replaced by NSGs.

TABLE I

| Semipeptoid no. (class) | structure | $IC_{50}$(FT) μM | $IC_{50}$(GGT) μM | alternative substrate | SEQ ID NO: |
|---|---|---|---|---|---|
| 1 (I) | Cys-Val-NGly-Met (benzyl) | 0.10 | 40 | no | 5 |
| 2 (I) | Cys-Val-NGly-Met (phenethyl) | 0.32 | 30 | no | 6 |
| 3 (I) | Cys-Val-NGly-Met (3,4-dimethoxyphenethyl) | 0.12 | 23 | no | 7 |
| 4 (I) | Cys-Val-NGly-Met (cyclohexyl) | 0.07 | 5 | no | 8 |
| 5 (II) | Cys-NGly-NGly-Met (isobutyl, phenethyl) | 13 | 190 | no | 9 |
| 6 (II) | Cys-NGly-NGly-Met (isobutyl, 3,4-dimethoxyphenethyl) | 4 | 80 | no | 10 |
| 7 (II) | Cys-NGly-NGly-Met (dimethylaminoethyl, benzyl) | 3 | 40 | no | 11 |

TABLE I-continued

| Semipeptoid no. (class) | structure | IC$_{50}$(FT) μM | IC$_{50}$(GGT) μM | alternative substrate | SEQ ID NO: |
|---|---|---|---|---|---|
| 8 (III) | Cys-NGly-Phe-Met (isopropyl side chain) | 50 | 155 | no | 12 |
| 9 (III) | Cys-NGly-Phe-Met (N-ethyl side chain) | 4 | >400 | no | 13 |
| 10 (III) | Cys-NGly-Phe-Met (isobutyl side chain) | 75 | 240 | no | 14 |
| 11 | Cys-NVal-NGly-Met (cyclohexyl side chain) | 0.0012 | 0.91 | no | 15 |

Figure 3:
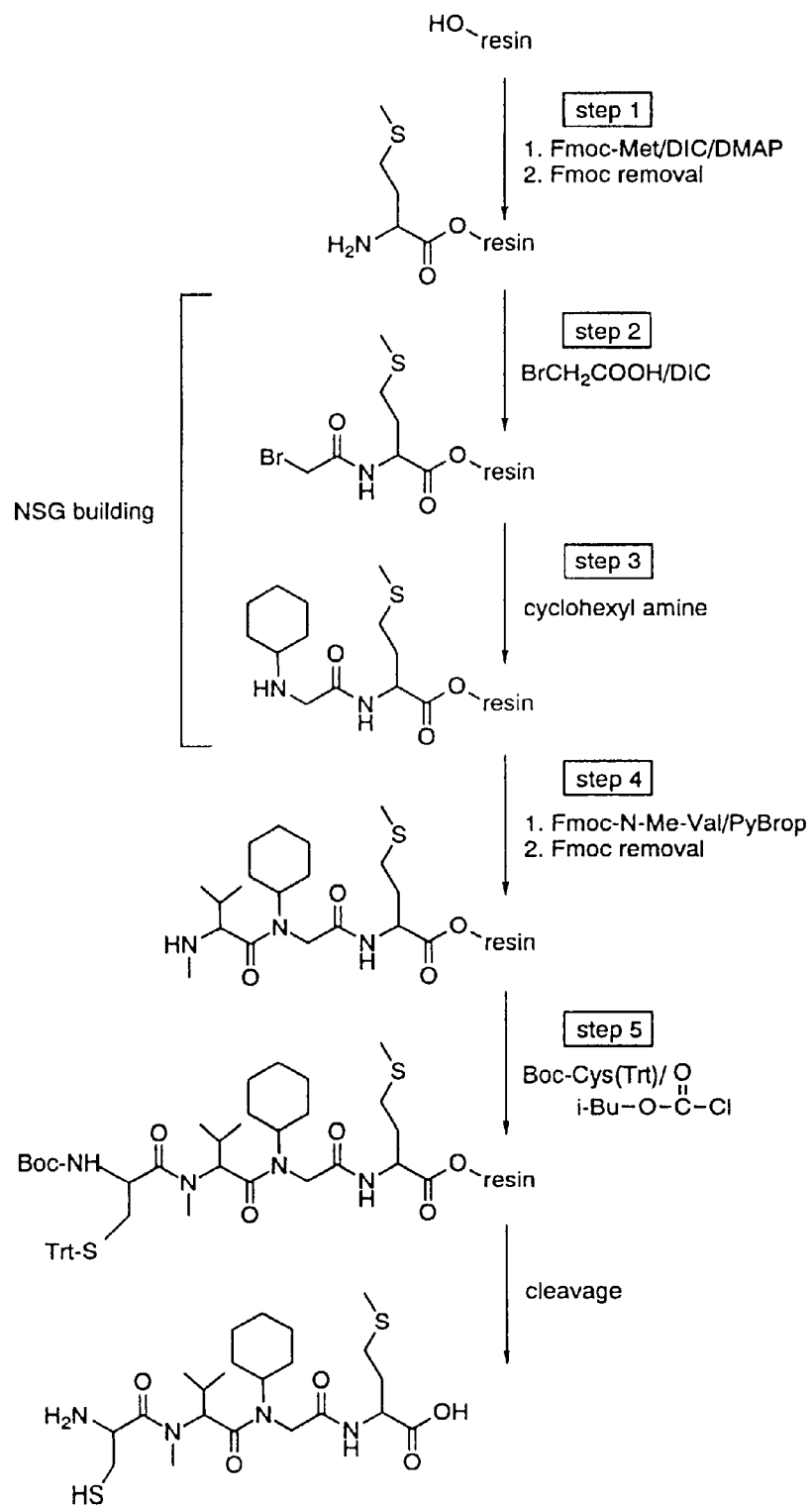
FIG. 3 is a schematic depiction of stages in the synthesis of cysteinyl-(Nα-methyl)valyl-(Nα-cyclohexyl)glycyl-methionine (i.e., compound 11, SEQ ID NO:15) according to the present invention.

FIG. 3 exemplifies the sequential synthetic steps for building compound 11, the most potent and selective semipeptoid FT-inhibitor. Semipeptoid 11 synthesis includes all the coupling types used for preparation of compounds 1–10. The NSG units of the semipeptoids were built on the resin via the "submonomer" synthesis reported by Zuckermann (Zuckermann et al., J. Am. Chem. Soc., 1992, 114: 10646). Each cycle of monomer addition consisted of two steps, an acylation step followed by a nucleophilic displacement step. Coupling of bromoacetic acid to the resin-bound amine was performed by N,N'-diisopropyl carbodiimide (DIC) (step 2, FIG. 3). In the second step the side chain was introduced by nucleophilic substitution of the bromide with an excess of alkyl or aryl amine (step 3, FIG. 3). N-protected amino acids were coupled using various coupling reagents, depending on the steric hindrance of the amine attached to the peptide-resin. Bromo-tris-pyrrolidino-phosphonium hexafluorophosphate (PyBroP) was used for coupling of N-protected amino acids to the secondary amine of the NSG units (step 4, FIG. 3). In the problematic attachment of N-protected amino acid to the secondary amine of the N-Me-Val, PyBroP was replaced by the mixed anhydride activation method with isobutyl chloroformate (step 5, FIG. 3) (Anderson et al., J. Amer. Chem. Soc., 1967, 89: 5012).

Biological Assays

An effective inhibitor must show high affinity and high selectivity towards the target enzyme, but must not serve as an alternative substrate if its product is less potent. These qualities were tested in vitro for the semipeptoid FT inhibitors described in the present invention.

The first assay determined the concentration needed for 50% inhibition (IC$_{50}$). FT activity was quantified by measuring the incorporation of [$^3$H]farnesyl from all-trans-[$^3$H]farnesylpyrophosphate into purified Gst-HRas.

The second assay estimated the selectivity of the inhibitor towards FT over a related enzyme, geranylgeranyl-protein-transferase-I (GGT), which transfers a C$_{20}$-isoprenoid to a thiol group of cysteine of a C-terminal CAAL (SEQ ID NO:17) peptide sequence derived from geranylgeranylpyrophosphate. Geranylgeranylation of normal cellular proteins is 5–10 times more common than farnesylation (Gibbs et al., Cell, 1994, 77: 175; Gibbs, Cell, 1991, 65: 1; Maltese,. FASEB J., 1990, 4: 3319).

A selective FT-inhibitor is considered to cause fewer cytotoxic effects than a nonselective inhibitor of both FT and GGT. GGT activity, for the partially purified GGT enzyme (Moores et al., J. Biol. Chem., 1991, 266: 14603), was quantified by measuring the incorporation of [$^3$H]geranylgeranyl from all trans [$^3$H]geranylgeranylpyrophosphate, into purified Gst-HRas-CVLL.

The third assay checked whether the inhibitor itself undergoes farnesylation. For this purpose, the inhibitor was incubated with the FT enzyme and [$^3$H]farnesylpyrophosphate in the absence of Ras. It has been shown previously that farnesylated-CAAX-peptides (SEQ ID NO:1) were about 13-fold (for CVLS (SEQ ID NO:18)) or 16-fold (for CVIM, SEQ ID NO:19) less potent as inhibitors than their corresponding tetrapeptides (Goldstein et al., J. Biol. Chem. 1991, 266: 15575; EP 0 461 869 A2 to Gibbs).

In the fourth assay, the most effective inhibitor derived from the in vitro screen was methyl esterified and subjected to intact cells, to examine its effect on Ras processing. Its selectivity towards FT as compared to GGT in whole cells, was determined by its relative inhibitory effects on Ras farnesylation and on Rap1A/Krev geranylgeranylation (Casey, J. Lipid Res. 1992, 33, 1731–1740; Cox et al., Curr. Opin. Cell Biol. 1992, 4, 1008–1016; Garcia et al., J. Biol. Chem. 1993, 268, 18415–18418; and Vogt et al., J. Biol. Chem. 1995, 270, 660–664), respectively. v-Ha-ras transformed NIH3T3 cells were incubated with lovastatin or increasing concentrations of the inhibitor. Cells were lysed and the processed and unprocessed forms of Ras or Rap1A were separated by SDS-PAGE and immunoblotted with anti-Ras or anti-Rap1A antibodies, respectively. Lovastatin is a compound which blocks the processing of isoprenylated proteins in cells by inhibiting an early step of the isoprenoid biosynthetic pathway, and therefore serves as a positive control for the inhibition of both geraylgeranylation and farnesylation (Kohl et al., Science 1993, 260, 1934–1937; Garcia et al., J. Biol. Chem. 1993, 268, 18415–18418; Vogt et al., J. Biol. Chem. 1995, 270, 660–664).

Structure Activity Relationship

The results of the structure activity relationship studies of the FT-semipeptoid-inhibitors are shown in Table I. Comparing semipeptoids 1, 5 and 8 which have the same side chains enables to examine the importance of the location of the isopropyl and the benzyl side chains on the inhibitory activity. Each one of these semipeptoids represents a different class. In semipeptoid 1 (class I) the side chain of Phe is shifted to the nitrogen, in semipeptoid 8 (class III) the side chain of Val is shifted to the nitrogen, and in semipeptoid 5 (class II) both side chains are shifted. Semipeptoid 1 was found to be 130 and 500 fold more potent than compounds 5 and 8 respectively. Accordingly, compound 3 is 33 times more potent than compound 6.

Comparison of the $IC_{50}$ ranges of class I (compounds 1–4), class II (compounds 5–7) and class III (compounds 8–10) generalized the conclusion that when the Cys and Met are unmodified in the peptoid frame, the position of the side chain of the valine is critical for the inhibitory activity.

This is not the case, however, for the Phe side chain. CVFM, SEQ ID NO:16 ($IC_{50}$=50 nM) and compound 1 ($IC_{50}$=100 nM) showed similar activities towards FT. Thus, the benzyl side chain of these inhibitors might occupy the same binding pocket in FT, although its position in the peptide backbone is shifted. This is possible due to the increased flexibility of the peptoid chain compared to its parent compound. This explanation is corroborated by recent findings showing that replacing Phe with tetrahydroindole carboxylic acid (Tic), in which the benzyl side chain is attached to both Cα and Nα, improved the inhibitory activity (Clerc et al.,. J. Bioorg. Med. Chem. Lett., 1995, 5: 1779).

Among the FT inhibitors of class I, semipeptoid 4 was found to be the most potent one. It was suggested that introduction of NSG units replacing amino acid residues renders the peptide backbone achiral and flexible (Kessler, Angew. Chem. Int. Ed. Engl., 1993, 32: 543). The proximity of the bulky cyclohexyl side chain to the backbone in semipeptoid 4 imposes local conformational constraint that might compensate for the relative flexible character of compounds 1–3.

In addition, the length and/or aliphatic character of this specific side chain might fit better to the pocket in the active site of the FT enzyme. Extension by one methylene of the spacer connecting the phenyl and the peptide backbone reduced relative potency by 3.2 fold both in the peptoidic structure (compound 2 versus compound 1) and in the peptidic structure CV-HomoPhe-M versus CVPM, SEQ ID NO:16 (leftheris et al., Bioorg. Med. Chem. Lett., 1994, 4: 887). Moreover, it was found that in $CA_1A_2X$ (SEQ ID NO:1) FT-peptide-inhibitors, free terminal amine and an aromatic residue at $A_2$ are essential to prevent farnesylation of the inhibitor (Brown et al., Proc. Natl. Acad. Sci. USA, 1992, 89: 8313). Interestingly, upon shifting the side chain at $A_2$ to the backbone nitrogen, aromaticity was no longer required to preclude the inhibitor from becoming an alternative substrate.

One of the aims of the peptoid approach is the introduction of N-alkylated peptide bonds that increases metabolic stability. Semipeptoid 4 has one N-alkylated peptide bond at the $A_1$–$A_2$ position. Almost any modification of the C-terminal Phe-Met peptidic bond that has been attempted, e.g. N-methylation or reduction to methyleneamine (leftheris et al., Bioorg. Med. Chem. Lett., 1994, 4: 887), led to a decrease of inhibition potency, suggesting that either the Phe-Met amide bond is involved in a critical hydrogen bond or a certain geometry is required at this position (leftheris et al., Bioorg. Med. Chem. Lett., 1994, 4: 887).

The most effective FT inhibitors reported previously posses the original Phe-Met peptide bond (Kohl et al., Science, 1993, 260: 1934; James et al., Science, 1993, 260: 1937; Kohl et al., Nature Medicine, 1995, 1: 792; Garcia et al., J. Biol. Chem., 1993, 268: 18415).

On the other hand the N-terminal Cys-Val bond showed wide tolerance towards structural modifications. A number of studies have already shown increased potency due to reduction of this amide to methyleneamine (Kohl et al., Science 1993, 260: 1934; leftheris et al, Bioorg. Med. Chem. Lett., 1994, 4: 887; Garcia et al., J. Biol. Chem., 1993, 268: 18415). N-methylation of this peptide bond led to a decreased potency of the CVFM peptide, SEQ ID NO:16 (leftheris et al., Bioorg. Med. Chem. Lett., 1994, 4: 887) but improved the inhibition activity of CAAX (SEQ ID NO:1) peptidomimetics bearing a local conformational constraint (James et al., Science, 1993, 260: 1937).

N-methylation of compound 4 at that position (yielding compound 11) improved its potency 58 fold ($IC_{50}$=1.2 nM), increased its selectivity 11 fold ($IC_{50}$(GGT)/$IC_{50}$(FT)=758) and preserved it as a non-farnesylated inhibitor. This modification aims to improve the inhibitor metabolic resistance and to increase its hydrophobicity in order to turn it available for FT inhibition in intact cells.

In the semipeptoid structure, shifting the side chains from the Cα atom to the nitrogen of the peptidic backbone changes the orientation of the side chains in space. In order to maintain the relative orientation of the carbonyl groups and the side chains as in the original bioactive peptide it was suggested to build a retrosequence in which the direction of the peptide bonds are reversed. This structure was called 'retropeptoid' (Simon et al., Proc. Natl. Acad. Sci. USA, 1992, 89: 9367; Kessler, Angew. Chem. Int. Ed. Engl., 1993, 32: 543). The application of the retropeptoid approach to linear peptides having free amino and carboxyl end groups arises the problem of topological uncomplementary of the end groups, first observed in linear retro-inverso peptides (Goodman and Chorev, Acc. Chem. Res., 1978, 12: 1). FIG. 1 shows the topological relation between a tetrapeptide, its semipeptoid and its retropeptoid analogs. One can observe that while in the semipeptoid the free amino and the carboxy termini are aligned with the parent peptide, side chains $R_2$ and $R_3$ are not. In the retropeptoid, the side chains and backbone carbonyls have the same topology as in the parent peptide, however, the end groups mismatch and the terminal amine is alkylated.

In CAAX (SEQ ID NO:1) inhibitors this creates a problem as the topological alignment of the carboxy and amino terminals as free groups is assumed to be critical for the inhibitory activity.

For example, acylation or methylation of the $NH_2$ group reduced potency and turned the inhibitor into an alternative substrate (Brown et al., Proc. Natl. Acad. Sci. USA, 1992, 89: 8313; leftheris et al., Bioorg. Med. Chem. Lett., 1994, 4: 887; Marsters et al., Bioorg. Med. Chem., 1994, 2, 949).

Esterification decreases the in vitro affinity of the inhibitor to farnesyltransferase as well. In cultured cells and in animals the ester derivatives have enhanced farnesyl transferase inhibitory potency.

The tetrapeptide analog L-731,735 (N-{2(S)-[2(R)-amino-3-mercaptopropylamino]-3(S)-methylpentyl}isoleucyl-homoserine, SEQ ID NO:20) is a potent and selective inhibitor of farnesyl protein transferase in vitro. In contrast, a prodrug of this compound, the related lactone compound L-731,734 (N-{2(S)-[2(R)-amino-3-mercaptopropylamino]-3(S)-methylpentyl}isoleucyl-homoserine lactone, SEQ ID NO:21), is less potent in inhibiting the farnesyl protein transferase activity in vitro, suggesting that the COOH-terminal carboxylate is an important determinant of the intrinsic farnesyl protein transferase inhibitory potency (Kohl et al., Science, 1993, 260, 1934). On the other hand L-731,734 (the lactone derivative) is capable of efficiently inhibit Ras processing in cells transformed with v-ras, by decreasing the ability of v-ras-transformed cells to form colonies in soft agar. Compound L-731,735 has no effect on Ras processing in cells transformed with v-ras. The specificity of inhibition by L-731,734 is demonstrated by the fact that the compound has no effect on the efficiency of colony transformation of cells transformed by either v-raf or v-mos oncogenes.

Another class of farnesyl transferase inhibitor, "benzodiazepin peptidomimetics", consists of CAAX tetrapeptide analogs (SEQ ID NO:1), in which the aliphatic AA portion of CAAX (SEQ ID NO:1) is replaced with 3-amino-1-carboxyl-methyl-5-phenyl-benzodiazepin-2-one, referred to as BZA scaffold (James et al., Science 1993, 260: 1937). BZA scaffold mimic a natural dipeptide turn. Compound BZA-2B is one of the compound of this series and has strong farnesyl transferase inhibitory potency. Compound BZA-5B is derived from compound BZA-2B by COOH-terminal esterification. In vitro, BZA-2B exhibits a less inhibitory potency than BZA-2B. However, in met18b-2 cells, BZA-5B (the methyl ester derivative) is a much more potent inhibitor than the parent compound BZA-2B.

As reported above peptidomimetic compound L-739,749 (2(S)-[2(CH(CH$_3$)$_2$)-amino-3-mercapto]-propylamino-3(S)-methyl]pentyloxy-3-phenylpropionyl methionine sulphone methyl ester, SEQ ID NO:2) is a potent farnesyl protein transferase inhibitor (Kohl et al., Proc. Natl. Acad. Sci. USA, 1994, 91: 9141). This compound is the methyl ester of compound L-739,750 (2(S)-[2(CH(CH$_3$)$_2$)-amino-3-mercapto]-propylamino-3(S)-methyl]pentyloxy-3-phenylpropionyl methionine sulphone SEQ ID NO:4). Compound L-739,750 is a potent inhibitor of protein farnesyl transferase in vitro. Compound L-739,749, the methyl ester, is a moderate inhibitor of protein farnesyl transferase in vitro. On the other hand, compound L-739,749 exhibits a superior inhibitory activity in cells, as compared to compound L-739,750.

In summary, the above reported results indicate the following. First, The COOH-terminal carboxylate is an important determinant of the farnesyl protein transferase inhibitory potency. Second, masking of the C-terminal carboxylate facilitates entry of the drug into mammalian cells.

An additional example for the use of ester derivatives of peptide drugs is provided by Bodor et al. (Bodor et al., Science, 1992, 257: 1698). The enkephalins are sensitive to cleavage by endopeptidases. Cholesterol, a bulky and lipophilic steroid moiety, provides an ester function that increases the lipid solubility and also protects the COOH-terminal portion of the peptide from endopeptidase digestion.

Amidation (Pompliano et al., Biochemistry, 1992, 31: 3800) of the carboxy group decreases the affinity of the inhibitor to farnesyl transferase, as well. Moreover, topological changes of the carboxy group in relation to the thiol markedly reduce the inhibitory activity (leftheris et al., Bioorg. Med. Chem. Lett., 1994, 4: 887; Vogt et al., J. Biol. Chem., 1995, 270: 660). These considerations together with the thiol and the methionine requirements have led us initially to keep the cysteine/methionine frame untouched and to modify only the A$_1$A$_2$ spacer.

Figure 4A:
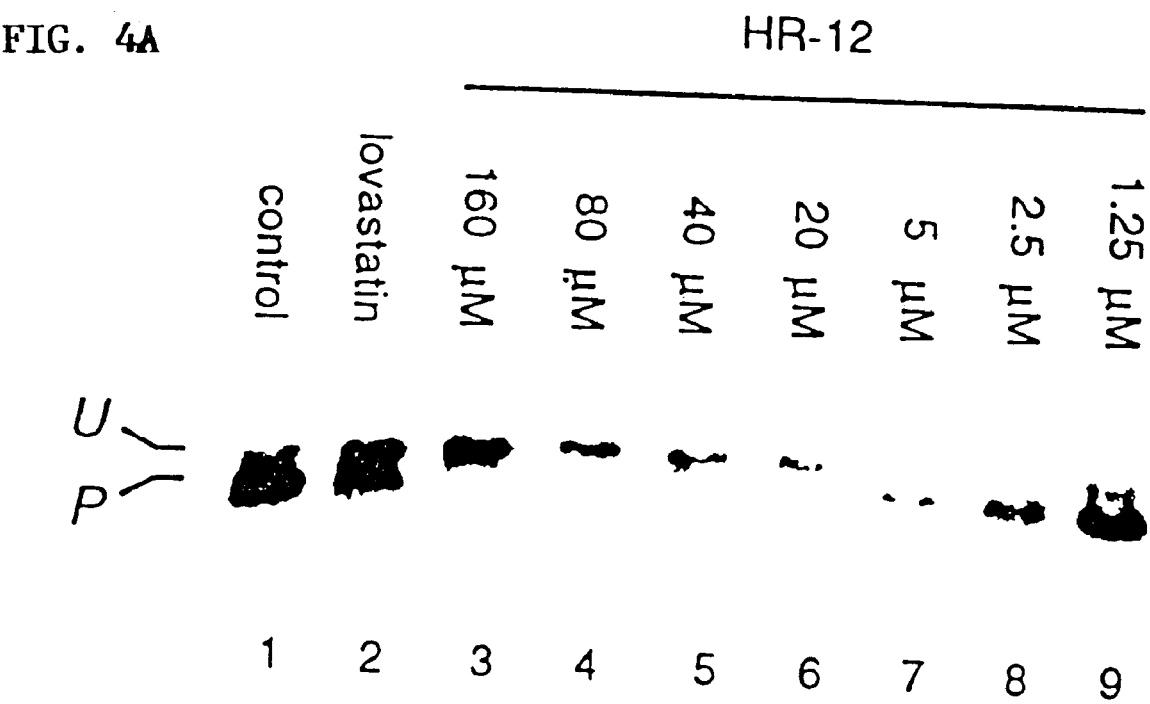
FIGS. 4a and 4b are western blots demonstrating effect of compound 12 on post-translational processing of Ras and Rap1A/K-rev, respectively. v-Ha-ras transformed NIH3T3 cells were treated by lovastatin (15 μM) or the indicated concentrations of compound 12, for 48 hr. Cell extracts were separated by SDS-PAGE (40 μg of protein/lane) and visualized by western blot as described under Example 19, wherein P is processed protein and U is unprocessed protein.

As mentioned, in order for FT inhibitors to become potential anti-cancer drugs they must exhibit metabolic stability, cellular permeability and retention of their selectivity towards FT, thus minimizing their toxic effects. Towards this end, v-ras transformed NIH3T3 cells were treated with compound 12, a methyl ester derivative of compound 11. This prodrug strategy (Kohl et al., Science 1993, 260, 1934–1937; James et al. Science 1993, 260, 1937–1942; Kohl et al., Proc. Natl. Acad. Sci. USA 1994, 91, 9141–9145; and Vogt, A.; Qian et al., J. Biol. Chem. 1995, 270, 660–664) masks the negative charge of the free carboxylate, thereby enables it to penetrate the cell membrane. After hydrolysis by cellular esterases the activated inhibitor is generated and trapped within the cell. After 48 hr of incubation, cell extracts were separated on SDS-PAGE and immunoblotted with anti-Ras antibody. Unprocessed Ras migrates slower than its processed form on SDS-PAGE (Kohl et al., Science 1993, 260, 1934–1937; James et al., Science 1993, 260, 1937–1942; Garcia et al., J. Biol. Chem. 1993, 268, 18415–18418; Vogt et al., J. Biol. Chem. 1995, 270, 660–664; and Graham J. Med. Chem. 1994, 37, 725–732). FIG. 4a shows increased amount of unprocessed Ras versus processed Ras in cells treated with lovastatin (lane 2) in comparison to cells treated with vehicle (lane 1). A dramatic effect is observed in the presence of compound 12 (lanes 3–9), which causes a dose dependent shift of Ras towards its unprocessed form at a concentration range of 1–160 mM, with an in situ IC$_{50}$ of 10 mM.

Figure 4B:
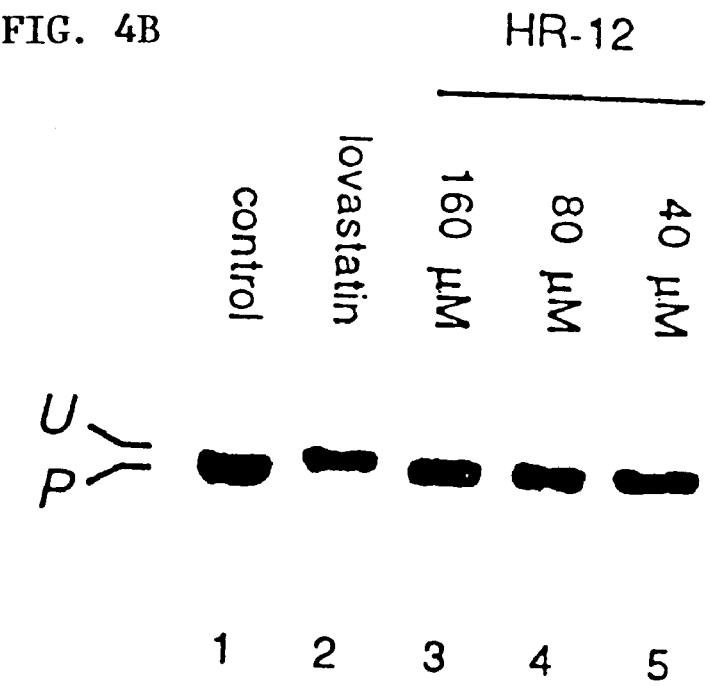

To test the selectivity of compound 12 towards FT in whole cells, the post-translational processing of an endogenous geranylgeranylated protein, Rap1A/K-rev, was analyzed. FIG. 4b shows that Rap1A/K-rev processing was not affected by compound 12 over the same concentration range (lanes 3–5). In contrast, lovastatin did inhibit Rap1A/K-rev processing, as indicated by a slight shifting of the Rap1A band upward (lane 2). These results clearly demonstrate that compound 12 selectively inhibits farnesylation but not geranylgeranylation. The lack of toxic effects of compound 12 up to 250 mM (data not shown) may be at least partially attributed to its high selectivity towards FT as compared to GGT. Moreover, the lack of inhibition of Rap1A/K-rev by compound 12 is advantageous, since Rap1 is a suppressor of Ras signaling (Kitayama et al. Cell 1989, 56, 77–84).

Thus, according to the present invention provided is a peptidornimetic compound, which is an inhibitor of farnesyl protein transferase and includes a peptoid analog (e.g., a semipeptoid analog) of farnesyl protein transferase recognition tetrapeptide sequence motif CA$_1$A$_2$X (SEQ ID NO:1). The compound may include at least one backbone chemical modification such as Nα-alkylation or Cα-alkylation.

Examples of alkylations include but are not limited to methylation, haloalkylation, alkenylation, cycloalkylation, alkoxyalkylation, arylalkylation, aminoalkylation, carboxyalkylation, carboalkoxyalkylation, carbamylation, carbamylalkylation, guanidinolation, guanidinoalkylation, mercaptolation, mercaptoalkylation, alkylthiolation, alkylthioalkylation, imidazolylation, imidazolalkylation, pyridylation, pyridylalkylation, piperidylation, piperidylalkylation, indolylation or indolyalkylation.

The semipeptoid compound according to the present invention may include native amino acid side chains (i.e., ones found in conventional amino acids) or chemically modified amino acid side chains, which are side chains not found in nature, yet many of which were previously linked at Cα or Nα positions of peptide backbones. Another way of describing native amino acid side chains and chemically modified amino acid side chains is to re-divide this collective group of side chains to side chains including alkyl moieties and side chains including aryl moieties. Examples of alkyl and aryl moieties include but are not limited to t-butyl, cyclohexyl, cyclohexyl derivatives, phenyl, phenyl derivatives, benzyl, benzyl derivatives, naphtyl, and naphtyl derivatives.

In a preferred embodiment of the invention, the native and chemically modified side chains are as follows: (a) sulfhydryl for the C; (b) isopropyl, N,N-dimethylaminoethyl and isobutyl for the $A_1$; (c) benzyl, phenethyl, 3,4-dimetoxyphenethyl and cyclohexyl for the $A_2$; and (d) hydroxyl and methyl for the X.

A different way of describing the preferred compounds according to the present invention is as follows. A peptidomimetic compound inhibitor of farnesyl protein transferase, including a chemical of the general formula C-$A_1(R_1)$-$A_2$($R_2$)-X (SEQ ID NO:1), wherein (a) the C is cysteinyl or N-substituted-glycine analog of cysteinyl; (b) the $A_1(R_1)$ is a first aliphatic amino-acid residue or N-substituted-glycine peptoid analog of the first aliphatic amino-acid residue, the $R_1$ is a native first side chain of the first aliphatic amino-acid residue or a chemical modification of the native first side chain; (c) the $A_2(R_2)$ is a second aliphatic amino-acid residue or N-substituted-glycine peptoid analog of the second aliphatic amino-acid residue, the $R_2$ is a native second side chain of the second aliphatic amino-acid residue or a chemical modification of the native second side chain; (d) the X is methionine, serine, R substituted ethionine, N-substituted-glycine peptoid analog of methionine, N-substituted-glycine peptoid analog of methionine, N-substituted-glycine peptoid analog of R substituted ethionine sulfoxide methionine, sulfoxide serine, sulfoxide R substituted ethionine, suffoxide N-substituted-glycine peptoid analog of methionine, sulfoxide N-substituted-glycine peptoid analog of methionine, suffoxide N-substituted-glycine peptoid analog of R substituted ethionine, sulfone methionine, sulfone serine, sulfone R substituted ethionine, sulfone N-substituted-glycine peptoid analog of methionine, sulfone N-substituted-glycine peptoid analog of methionine or sulfone N-substituted-glycine peptoid analog of R substituted ethionine; and (e) the compound includes at least one N-substituted-glycine analog.

In a preferred embodiment, the first and second aliphatic amino-acid residues are valyl, phenylalanyl, alanyl leucinyl or isoleucinyl, and the N-substituted-glycine peptoid analogs of the first and second aliphatic amino-acid residues are selected from the group consisting of (Nα-isopropyl)glycyl and (Nα-phenethyl)glycyl.

In another preferred embodiment, the native first and second side chains of the first and second aliphatic amino-acid residues are selected from the group consisting of isopropyl and phenethyl, and the chemical modification of the native first and second side chains are selected from the group consisting of N,N-dimethylaminoethyl, isobutyl, benzyl, 3,4-dimetoxyphenethyl and cyclohexyl.

Yet, another way of describing the preferred compounds according to the present invention is as follows. A peptidomimetic compound inhibitor of farnesyl protein transferase including a chemical of the general formula C-$A_1$-$A_2$-X (SEQ ID NO:1), wherein: (a) the C is cysteinyl or N-substituted-glycine analog of cysteinyl; (b) the $A_1$ a first C-alkyl-substituted-glycine, a first C-aryl-substituted-glycine, a first N-alkyl-substituted-glycine or a first N-aryl-substituted-glycine; (c) the $A_2$ is a second C-alkyl-substituted-glycine, a second C-aryl-substituted-glycine, a second N-alkyl-substituted-glycine or a second N-aryl-substituted-glycine; (d) the X is methionine, serine, N-substituted-glycine analog of methionine or N-substituted-glycine analog of methionine; and (e) the compound includes at least one N-substituted-glycine.

In a preferred embodiment, the first and second C-alkyl-substituted-glycine are each selected from the group consisting of valyl, (Cα-isopropyl)glycyl, (Cα(N,N-dimethylaminoethyl))glycyl and (Cα-isobutyl)glycyl.

In another preferred embodiment, the first and second N-alkyl-substituted-glycine are each selected from the group consisting of valyl, (Nα-isopropyl)glycyl, (Nα(N,N-dimethylaminoethyl))glycyl and (Nα-isobutyl)glycyl.

In yet another preferred embodiment, the first and second C-aryl-substituted-glycine are each selected from the group consisting of phenylalanyl, (Cα-benzyl)glycyl, (Cα-3,4-dimetoxyphenethyl)glycyl and (Cα-cyclohexyl)glycyl.

In yet another preferred embodiment, the first and second N-aryl-substituted-glycine are each selected from the group consisting of phenylalanyl, (Nα-benzyl)glycyl, (Nα-3,4-dimetoxyphenethyl)glycyl and (Nα-cyclohexyl)glycyl.

According to a preferred embodiment, the peptoid peptidomimetic compound, which is an inhibitor of farnesyl protein transferase and includes a semipeptoid analog of farnesyl protein transferase recognition tetrapeptide sequence motif, further includes a C-terminus hydrophobic moiety such as but not limited to an ester moiety such as alkyl ester or aryl ester, for example, methyl ester, ethyl ester, hydroxyetlyl ester, t-butyl ester, cholesteryl ester, isopropyl ester or glyceryl ester.

The compounds herein described may be used as a chemotherapeutic treatment which includes administration of any of the compounds to a living creature, such as a human, for inhibition of farnesyl protein transferase in oncogenic or non-oncogenic Ras associated cancers and proliferative diseases.

The present invention teaches the properties of semipeptoids as possible drugs in the treatment of certain cancers. The structure of these molecules mimics the carboxyl terminus of the protein farnesyl transferase and they inhibit the in vitro activity of the enzyme. Protein farnesyl transferase is known to catalyzes post-translational modifications of Ras proteins required for cell transformation by Ras oncoprotein. Esterification of tetrapeptide drugs, known to be protein farnesyl transferase inhibits, has been shown to enhance in vivo the inhibitory effects of these drugs. This enhancement is probably due to increased stability of the drugs and increased permeability of drugs through the cell membrane. Therefore, it is apparent to one to synthesize the ester derivatives of the semipeptoids described in the present invention, in order to enhance their in vivo inhibitory potency and use them as potent in vivo inhibitors of protein farnesyl transferase.

Reference is now made to the following examples, which together with the above descriptions, illustrate the invention.

EXAMPLE 1

General Procedure for the Synthesis of Semipeptoids 1–10

Figure 2:
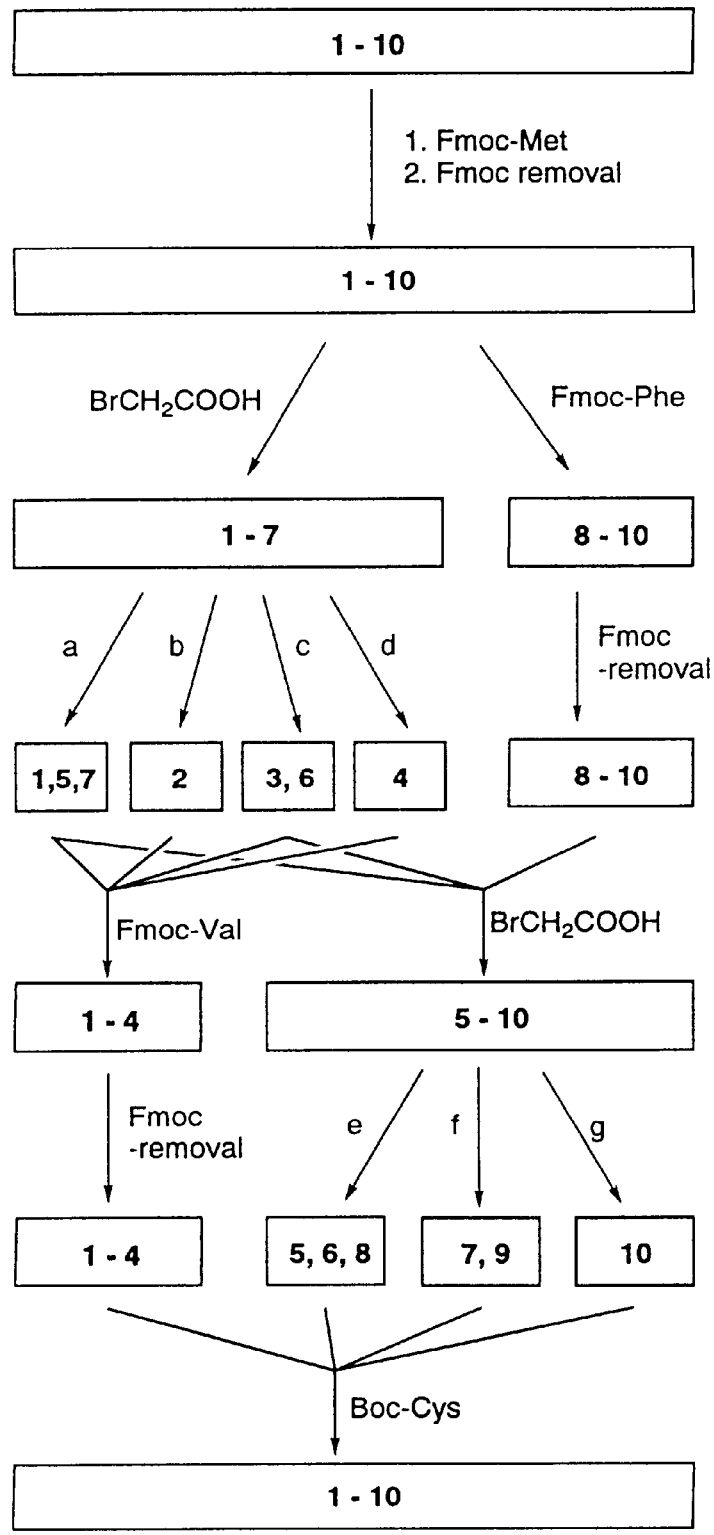
FIG. 2 is a schematic depiction of the synthesis of compounds 1–10 according to the present invention by the simultaneous multiple analog peptide synthesis using the "tea bags" approach, wherein amines used are a=benzylamine, b=phenethylamine, c=3,4-dimethoxyphenethylamine, d=cyclohexylamine, e=isopropylamine, f=N,N-dimethylethylenediamine, and g=isobutylamine.

Solid phase peptide synthesis was performed according to the general Merrifield synthetic protocols (Fields et al, Int. J. Pept. Protein Res. 1989, 35: 161, incorporated by reference as if fully set forth herein). After each step the peptide resin was washed with DMF (3 times), dichloromethane (2 times) and DMF (3 times). After deprotection of Met, Phe and Val and coupling to their primary amines, Kaiser test was performed to ensure deprotection and full coupling (Kaiser et al., Anal. Biochem. 1970, 34: 595). The library was synthesized by the simultaneous multiple solid phase analog peptide synthesis (MAPS) method (Houghten,. Proc. Natl. Acad. Sci. USA, 1985, 82: 5131), using the "tea bags" approach (see FIG. 2). The solid support (Wang resin, 0.93 meq/gr) was contained in 10 polypropylene mesh bags (100 mg resin per bag). After washing the resin, a mixture of Fmoc-Met (4 eq), DIC (4 eq) and dimethyl-amino-pyridine (0.16 eq) dissolved in DMF (80 ml) was added and shaken for 2 hours to give 0.5 meq coupled Fmoc-Met per gr resin, determined by quantitative Fmoc-Piperidine test (Meienhofer et al., Int. J. Pept. Protein Res., 1979, 13: 35). The remaining OH-groups on the resin were capped (acetic acid anhydride (6 eq)/DMF, 30 minutes). Fmoc was removed from the resin by treatment with 30% piperidine/DMF for 20 minutes.

For clarity, in the following Examples 2–12 the synthetic process of each compound is described separately, although, as described above the "tea bags" approach was used. According to this method, synthesis of the compounds was carried out in polypropylene mesh bags. Bags undergoing the same synthetic step, were grouped and incubated in the same reaction vessel.

EXAMPLE 2

Synthesis of Semipeptoids 1 cysteinyl-valyl-(Nα-benzyl)glycyl-methionine (SEQ ID NO:5)

The N-alkylated-glycine units in compound 1 were built in two steps, an acylation step and a nucleophilic displacement step. The acylation reaction was performed by addition of a mixture of bromoacetic acid (30 eq) and DIC (33 eq) in DMF (70 ml), to a vessel containing bag 1. The reaction mixture was shaken for 30 minutes. The acylation procedure was repeated once. After washings, the displacement reaction was performed by addition of benzylamine as a 2.5 M solution in dimethylsulfoxide (DMSO), and agitation for 2 hours.

Fmoc-Val was coupled to the secondary amines of compound 1 by shaking the bag with a preactivated mixture of Fmoc-Val (6 eq), PyBroP (6 eq) and DIEA (12 eq) in DMF (35 ml) for 2 hours, followed by Fmoc- removal.

The bag was then agitated with a preactivated mixture of 80 ml of DMF containing Boc-Cys(Trt) (6 eq), PyBroP (6 eq) and DIEA (12 eq) overnight.

EXAMPLE 3

Synthesis of Semipeptoids 2 cysteinyl-valyl-(Nα-phenethyl)glycyl-methionine (SEQ ID NO:6)

The N-alkylated-glycine units in compound 2 were built in two steps, an acylation step and a nucleophilic displacement step. The acylation reaction was performed by addition of a mixture of bromoacetic acid (30 eq) and DIC (33 eq) in DMF (70 ml), to a vessel containing bag 2. The reaction mixture was shaken for 30 minutes. The acylation procedure was repeated once. After washings, the displacement reaction was performed by addition of phenethylamine as a 2.5 M solution in dimethylsulfoxide (DMSO), and agitation for 2 hours.

Fmoc-Val was coupled to the secondary amines of compound 2, by shaking the bag with a preactivated mixture of Fmoc-Val (6 eq), PyBroP (6 eq) and DIEA (12 eq) in DMF (35 ml) for 2 hours, followed by Fmoc- removal.

The bag was then agitated with a preactivated mixture of 80 ml of DMF containing Boc-Cys(Trt) (6 eq), PyBroP (6 eq) and DIEA (12 eq) overnight.

EXAMPLE 4

Synthesis of Semipeptoids 3 cysteinyl-valyl-(Nα-3, 4-dimetoxyphenethyl)glycyl-methionine (SEQ ID NO:7)

The N-alkylated-glycine units in compound 3 were built in two steps, an acylation step and a nucleophilic displacement step. The acylation reaction was performed by addition of a mixture of bromoacetic acid (30 eq) and DIC (33 eq) in DMF (70 ml), to a vessel containing bag 3. The reaction mixture was shaken for 30 minutes. The acylation procedure was repeated once. After washings, the displacement reaction was performed by addition of 3,4-dimethoxyphenethyl amine as a 2.5 M solution in dimethylsulfoxide (DMSO), and agitation for 2 hours.

Fmoc-Val was coupled to the secondary amines of compound 3 by shaking the bag with a preactivated mixture of Fmoc-Val (6 eq), PyBroP (6 eq) and DIEA (12 eq) in DMF (35 ml) for 2 hours, followed by Fmoc- removal.

The bag was then agitated with a preactivated mixture of 80 ml of DMF containing Boc-Cys(Trt) (6 eq), PyBroP (6 eq) and DIEA (12 eq) overnight.

EXAMPLE 5

Synthesis of Semipeptoids 4 cysteinyl-valyl-(Nα-cyclohexyl)glycyl-methionine (SEQ ID NO:8)

The N-alkylated-glycine units in compound 4 were built in two steps, an acylation step and a nucleophilic displacement step. The acylation reaction was performed by addition of a mixture of bromoacetic acid (30 eq) and DIC (33 eq) in DMF (70 ml), to a vessel containing bag 4. The reaction mixture was shaken for 30 minutes. The acylation procedure was repeated once. After washings, the displacement reaction was performed by addition of cyclohexyl amine as a 2.5 M solution in dimethylsulfoxide (DMSO), and agitation for 2 hours.

Fmoc-Val was coupled to the secondary amines of compound 4, by shaking the bag with a preactivated mixture of Fmoc-Val (6 eq), PyBroP (6 eq) and DIEA (12 eq) in DMF (35 ml) for 2 hours, followed by Fmoc- removal.

The bag was then agitated with a preactivated mixture of 80 ml of DMF containing Boc-Cys(Trt) (6 eq), PyBroP (6 eq) and DIEA (12 eq) overnight.

EXAMPLE 6

Synthesis of Semipeptoids 5 cysteinyl-(Nα-isopropyl)glycyl-(Nα-benzyl)glycyl-methionine (SEQ ID NO:9)

The N-alkylated-glycine units in compound 5 were built in two steps, an acylation step and a nucleophilic displacement step. The acylation reaction was performed by addition of a mixture of bromoacetic acid (30 eq) and DIC (33 eq) in DMF (70 ml), to a vessel containing bag 5. The reaction mixture was shaken for 30 minutes. The acylation procedure was repeated once. After washings, the displacement reaction was performed by addition of benzylamine as a 2.5 M solution in dimethylsulfoxide (DMSO), and agitation for 2 hours.

The N-alkyl-glycine units in compound 5 were built by the same procedure described above with isopropyl amine.

The bag was then agitated with a preactivated mixture of 80 ml of DMF containing Boc-Cys(Trt) (6 eq), PyBroP (6 eq) and DIEA (12 eq) overnight.

EXAMPLE 7

Synthesis of Semipeptoids 6 cysteinyl-(Nα-isopropyl)glycyl-(Nα-3,4-dimetoxyphenethyl)glycyl-methionine (SEQ ID NO:10)

The N-alkylated-glycine units in compound 6 were built in two steps, an acylation step and a nucleophilic displacement step. The acylation reaction was performed by addition of a mixture of bromoacetic acid (30 eq) and DIC (33 eq) in DMF (70 ml), to a vessel containing bag 6. The reaction mixture was shaken for 30 minutes. The acylation procedure was repeated once. After washings, the displacement reaction was performed by addition of dimethoxyphenethyl amine as a 2.5 M solution in dimethylsulfoxide (DMSO), and agitation for 2 hours.

The N-alkyl-glycine units in compound 6 were built by the same procedure described above with isopropyl amine.

The bag was then agitated with a preactivated mixture of 80 ml of DMF containing Boc-Cys(Trt) (6 eq), PyBroP (6 eq) and DIEA (12 eq) overnight.

EXAMPLE 8

Synthesis of Semipeptoids 7 cysteinyl-(Nα(N,N-dimethylaminoethyl))glycyl-(Nα-benzyl)glycyl-methionine (SEQ ID NO:11)

The N-alkylated-glycine units in compound 7 were built in two steps, an acylation step and a nucleophilic displacement step. The acylation reaction was performed by addition of a mixture of bromoacetic acid (30 eq) and DIC (33 eq) in DMF (70 ml), to a vessel containing bag 7. The reaction mixture was shaken for 30 minutes. The acylation procedure was repeated once. After washings, the displacement reaction was performed by addition of benzylamine as a 2.5 M solution in dimethylsulfoxide (DMSO), and agitation for 2 hours.

The N-alkyl-glycine units in compound 7 were built by the same procedure described above with N,N-dimethylethylenediamine.

The bag was then agitated with a preactivated mixture of 80 ml of DMF containing Boc-Cys(Trt) (6 eq), PyBroP (6 eq) and DIEA (12 eq) overnight.

EXAMPLE 9

Synthesis of Semipeptoids 8 cysteinyl-(Nα-isopropyl)glycyl-phenylalanyl-methionine (SEQ ID NO:12)

After Fmoc removal the bag containing for the synthesis of compound 8 was shaken with preactivated 30 ml DMF containing Fmoc-Phe (6 eq), BOP (6 eq) and diisopropyl ethylamine (DIEA, 12 eq) for 2 hours, followed by Fmoc deprotection.

The N-alkyl-glycine units in bag 8 were built in two steps, an acylation step and a nucleophilic displacement step. The acylation reaction was performed by addition of a mixture of bromoacetic acid (30 eq) and DIC (33 eq) in DMF (70 ml), to a vessel containing bag 8. The reaction mixture was shaken for 30 minutes. The acylation procedure was repeated once. After washings, the displacement reaction was performed by addition of isopropyl amine as a 2.5 M solution in dimethylsulfoxide (DMSO), and agitation for 2 hours.

The bag was then agitated with a preactivated mixture of 80 ml of DMF containing Boc-Cys(Trt) (6 eq), PyBroP (6 eq) and DIEA (12 eq) overnight.

EXAMPLE 10

Synthesis of Semipeptoids 9 cysteinyl-(Nα(N,N-dimethylaminoethyl))glycyl-phenylalanyl-methionine (SEQ ID NO:13)

After Fmoc removal the bag containing for the synthesis of compound 9 was shaken with preactivated 30 ml DMF containing Fmoc-Phe (6 eq), BOP (6 eq) and diisopropyl ethylamine (DIEA, 12 eq) for 2 hours, followed by Fmoc deprotection.

The N-alkyl-glycine units in bag 9 were built in two steps, an acylation step and a nucleophilic displacement step. The acylation reaction was performed by addition of a mixture of bromoacetic acid (30 eq) and DIC (33 eq) in DMF (70 ml), to a vessel containing bag 8. The reaction mixture was shaken for 30 minutes. The acylation procedure was repeated once. After washings, the displacement reaction was performed by addition of N,N-dimethylethylenediamine as a 2.5 M solution in dimethylsulfoxide (DMSO), and agitation for 2 hours.

The bag was then agitated with a preactivated mixture of 80 ml of DMF containing Boc-Cys(Trt) (6 eq), PyBroP (6 eq) and DIEA (12 eq) overnight.

EXAMPLE 11

Synthesis of Semipeptoids 10 cysteinyl-(Nα-isobutyl)glycyl-phenylalanyl-methionine (SEQ ID NO:14)

After Fmoc removal the bag containing for the synthesis of compound 10 was shaken with preactivated 30 ml DMF containing Fmoc-Phe (6 eq), BOP (6 eq) and diisopropyl ethylamine (DIEA, 12 eq) for 2 hours, followed by Fmoc deprotection.

The N-alkyl-glycine units in bag 10 were built in two steps, an acylation step and a nucleophilic displacement step. The acylation reaction was performed by addition of a mixture of bromoacetic acid (30 eq) and DIC (33 eq) in DMF (70 ml), to a vessel containing bag 10. The reaction mixture was shaken for 30 minutes. The acylation procedure was repeated once. After washings, the displacement reaction was performed by addition of isobutyl amine as a 2.5 M solution in dimethylsulfoxide (DMSO), and agitation for 2 hours.

The bag was then agitated with a preactivated mixture of 80 ml of DMF containing Boc-Cys(Trt) (6 eq), PyBroP (6 eq) and DIEA (12 eq) overnight.

EXAMPLE 12

Synthesis of Semipeptoids 11 cysteinyl-(Nα-methyl)valyl-(Nα-cyclohexyl)glycyl-methionine (SEQ ID NO:15)

The N-alkylated-glycine units in compound 11 were built in two steps, an acylation step and a nucleophilic displacement step. The acylation reaction was performed by addition of a mixture of bromoacetic acid (30 eq) and DIC (33 eq) in DMF (70 ml), to a vessel containing bag 11. The reaction mixture was shaken for 30 minutes. The acylation procedure was repeated once. After washings, the displacement reactions were performed by addition of cyclohexyl amine as a 2.5 M solution in dimethylsulfoxide (DMSO), and agitation for 2 hours.

Fmoc-Val was coupled to the secondary amines of compound 11 by shaking the bag with a preactivated mixture of Fmoc-N-methyl-Val(6 eq), PyBroP (6 eq) and DIEA (12 eq) in DMF (35 ml) for 2 hours, followed by Fmoc- removal.

The mixed anhydride activation method (Anderson, G. W.; Zimmerman, J. E.; Callahan, F. M. (1967) *J. Amer. Chem. Soc.*, 89, 5012) was used for the coupling of Boc-Cys(Trt) to the secondary amine of the N-Me-Val residue. Boc-Cys(Trt) (3 eq) and N-methyl-morpholine (3 eq) were dissolved in DMF (15 ml) and cooled to −15° C. Isobutyl chloroformate (3 eq) was added slowly under stirring at −15° C. After 1 minute the mixture was added to the resin-peptide and shaken for 8 hours. The coupling was repeated for 4 hours with freshly activated Boc-Cys(Trt).

EXAMPLE 13

Synthesis of Semipeptoids 12 methyl ester Derivative of cysteinyl-(Nα-methyl)valyl-(Nα-cyclohexyl)glycyl-methionine (SEQ ID NO:15)

Compound 12, the methyl ester derivative of compound 11, was synthesized on 2-methoxy-4-alkoxybenzyl alcohol resin (1 gr, 0.96 meq/gr). The assembly of the semipeptoid is the same as for compound 11. The compound was cleaved from the resin, retaining the Na-Boc-Cys protecting group, in 5% of TFA in DCM. The crude product was dissolved in methanol (5 ml), cooled on an ice bath, and a saturated solution of diazomethane ($CH_2N_2$) in diethylether was added dropwise until the pale yellow color of the diazomethane solution appeared. After evaporation of the solvent, the Boc protecting group was removed in a mixture of thioanisole/ethanedithiol/TFA as described for deprotection and cleavage of semipeptoids 1–10. Compound 12 was purified to >90% purity level by semipreparative RP-HPLC (gradient: 0–5 min 10% A,90% B, 5–65 min from 10% A,90% B to 75% A,25% B, flow 3 ml/min).

EXAMPLE 14

General Procedure for Cleavage of Oligomers from the Resin

Protecting groups (Boc, Trt) were removed and the oligomer was cleaved from the resin by treatment of each peptide-resin with 3 ml of a precooled mixture of thioanisole (5% v/v)/ethanedithiol (2.5% v/v)/trifluoro acetic acid (TFA, 92.5% v/v) for 2 hours at room temperature, followed by filtration and cold ether precipitation. The precipitate was washed 3 times with 40 ml of cold ether. After vortex and centrifugation the ether was decanted and pooled. The final washed precipitate was dried in vacuum, dissolved in 1 mM DTT/30% acetic acid and lyophilized. The pooled ether washings were evaporated to dryness and washed 3 times with 10 ml of cold ether. The precipitate was treated as above.

EXAMPLE 15

Purification of Semipeptoids

The semipeptoids were purified to >95% purity level by semipreparative RP-HPLC ($C_{18}$ Vydac column, type 218TP510, column size: 1.0×25 cm, particle size: 5 m, gradient: A=acetonitrile (0.1% TFA); B=water (0.1% TFA) detection 210 nm; 0–20 minutes 20% A, 80% B 20–40 minutes from 20% A, 80% B to 80% A, 20% B, flow 3 ml/min). The purified peptides were characterized by analytical RP-HPLC ($C_{18}$ Vydac column, type 218TP54, column size: 0.46×25 cm, particle size: 5 m, gradient: 0–5 minutes 20% A, 80% B 5–35 minutes from 20% A, 80% B to 80% A, 20% B, flow 1 ml/min). The pure peptoids were subjected to molecular weight determination by FAB-MS (TSQ-70, FINNIGAN). k' values and MS determinations of the semipeptoids are given in Table II below.

TABLE II

HPLC and MS Characterization of Compounds 1–12

| Semipeptoid no. | k'HPLC | MS calculated | MS found |
|---|---|---|---|
| 1 | 3.2 | 498 | 498 |
| 2 | 3.2 | 512 | 512 |
| 3 | 3.1 | 572 | 572 |
| 4 | 3.5 | 489 | 490 |
| 5 | 1.3 | 498 | 498 |
| 6 | 3.3 | 572 | 572 |
| 7 | 1.6 | 527 | 527 |
| 8 | 3.1 | 498 | 498 |
| 9 | 1.7 | 527 | 527 |
| 10 | 4.6 | 512 | 512 |
| 11 | 4.7 | 505 | 505 |
| 12 | 8 | 518 | 518 |

EXAMPLE 16

Farnesyl Protein Transferase (FT) Inhibition Assay

Partial purification of FT from bovine brain was performed essentially as described by Reiss at al. (Reiss et al, Cell, 1990, 62: 81), except that a fractogel DEAE column (150×16 mm, Merck) was used for the ion exchange chromatagraphy step. GST-HRas expression vector was constructed by cloning the Hras gene into a pGEX-1 vector, and expressed in *E. coli* strain TG1. The protein was purified using glutathione agarose (Sigma USA). FT inhibition assays were run in 96-well dishes in a reaction volume of 30 ml. The final reaction mixture contained 5 mM GST-HRas, 0.9 mM [$^3$H]farnesylpyrophosphate 20,000 dmp/pmol (NEN-Dupont), 1 mg of partially purified FT, 5 mM $MgCl_2$, 3 mM $ZnCl_2$, 40 mM TRIS.HCl pH 7.5, 60 mM NaCl, 1 mM DTT, 0.2 mM Glutathione, 0.03% Octyl-b-D-glucopyranoside, and serial dilutions of inhibitor.

Following incubation at 37° C. for 30 minutes the reactions were stopped by adding 100 ml of 4% sodium dodecyl sulfate (SDS) followed by 100 ml of 30% trichloroacetic acid (TCA). Plates were incubated for 100 minutes on ice, and the precipitates were filtered using a Millipore milliblot™-system (Millipore Corp., Bedford Mass.) with GF/C membranes. The wells were washed twice with 200 ml of 2% SDS/6% TCA and 7 times with 200 ml of 6% TCA. The filters were punched into 4 ml vials and dried at 70° C. for 10 minutes. 3 ml of scintillation fluid was added and radioactivity was monitored by scintillation counting. $IC_{50}$ values were resolved from dose-response curves of percent control versus log drug concentration, using the Regression program (Blackwell, UK). Each compound was tested 2–4 times.

EXAMPLE 17

Geranylgeranyl Transferase-I (GGT) Inhibition Assay

GGT was partially purified from bovine brain. Cytosol was prepared and GGT was isolated using a fractogel DEAE column (150×16 mm, Merck) with NaCl gradient, as for FT purification (see Example 15 above). Fractions containing the GGT activity were pooled and stored at −70° C. Hras gene was point mutated using an oligonucleotide directed in vitro mutagenesis system (Amersham version 2.1). The mutated Hras gene was cloned into the GST—frame of a pGEX-1 expression vector, expressed in *E. coli* strain TG1, and a fusion protein Gst-HRas-CVLL (SEQ ID NO:22) was purified on glutathione agarose. In order to determine the $IC_{50}$ values for GGT inhibition the same assay as for the FT inhibition was conducted, except for using 0.9 mM [$^3$H] geranylgeranylpyrophosphate 10,000 dpm/pmol (NEN-Dupont) and 5 mM Gst-HRas-CVLL (SEQ ID NO:22) as substrates and 6.8 mg of partially purified GGT for the enzyme of the reaction.

EXAMPLE 18

Inhibitor Farnesylation Assay

For examination whether the inhibitors undergo farnesylation a previously described procedure (Goldstein et al., J. Biol. Chem., 1991, 266: 15575) was used. Each reaction mixture contained the following components in a final volume of 15 ml: 40 mM TRIS.HCl pH 7.5, 67 mM NaCl, 5 mM $MgCl_2$, 7 mM $ZnCl_2$, 1 mM DTT, 0.07% (v/v) octyl-b-D-glucopyranoside, 20 pmol of [$^3$H] farnesylpyrophosphate 45,000 dpm/pmol, 4 mM peptide or peptoid, and 1 mg of partially purified FT. After incubation at 37° C. for 30 minutes, the entire reaction mixture was spotted onto an aluminum backed Silica Gel thin layer sheet (20×20 cm, Merck), and placed in a tank containing n-propyl-alcohol/ammonium hydroxide/water (6:3:1, v/v/v). The chromatogram was run for 4 hours, sprayed with EN$^3$HANCE (Dupont) and exposed to RX film (FUJI) for 4 days at −70° C.

EXAMPLE 19

Protein Processing Assay in Intact Cells v-Ha-ras transformed NIH3T3 fibroblasts were treated with 15 mM lovastatin or the indicated concentrations of compound 12 or vehicle (0.25 mM DTT, 0.25% DMSO), for 48 hr. Cells were lysed (Garcia et al., J. Biol. Chem. 1993, 268, 18415–18418) in 1% Nonidet P-40, 5 mM TRIS.HCl pH 8.0, 5 mM EDTA, 1 mM phenylmethylsulfonyl fluoride, 10 mg/ml aprotonin, 10 mg/ml soybean trypsin inhibitor and 313 mg/ml benzamidine. The lysate was separated by centriflgation and the supernatant used as cell extract. Total protein was separated by SDS-PAGE (40 mg/lane) in 15% acrylamide (0.4% bis-acrylamide) gels, transferred onto nitrocellulose (Schleicher & Schuell, optitran BA-S 85) and probed with anti-Ras antibody Y13-259, or monoclonal anti-Rap1A/K-rev antibody (transduction laboratories). The western blots were visualized using an enhanced chemiluminescence (ECL) detection system.

While the invention has been described with respect to a limited number of embodiments, it will be appreciated that many variations, modifications and other applications of the invention may be made.

What is claimed is:

1. A peptidomimetic compound inhibitor of farnesyl protein transferase, which is a semipeptoid analog of farnesyl protein transferase recognition CAAX tetrapeptide sequence motif of a formula:

$CA_1A_2X$ (SEQ ID NO:1)

wherein,

C is cysteinyl;

X is selected from the group consisting of methionine and serine residues;

$A_1$ is (Nα-alkyl)valyl; and $A_2$ is (Nα-cycloaliphatic)glycyl;

whereas, Nα are nitrogen atoms of a peptide backbone.

2. The compound of claim 1, wherein said (Nα-alkyl) valyl is (Nα-methyl)valyl.

3. The compound of claim 1, wherein said (Nα-cycloaliphatic)glycyl is (Nα-cyclohexyl)glycyl.

4. The compound of claim 2, wherein said (Nα-cycloaliphatic)glycyl is (Nα-cyclohexyl)glycyl.

5. The compound of claim 1, exhibiting 50% inhibition of farnesyl protein transferase at a 1.2 nanomolar concentration.

6. The compound of claim 1 exhibiting selective inhibition toward farnesyl protein transferase as compared to inhibition of geranylgeranyl protein transferase I, as determined by 50% inhibition assays.

7. The compound of claim 1, wherein said compound is cysteinyl-(Nα-methyl)valyl-(Nα-cyclohexyl)glycyl-methionine (SEQ ID NO:15).

8. The compound of any one of claims 1–7, comprising a C-terminus ester moiety.

9. The compound of claim 8, wherein said ester moiety is selected from the group consisting of alkyl ester and aryl ester.

10. The compound of claim 9, wherein said alkyl and aryl esters are selected from the group consisting of methyl ester, ethyl ester, hydroxyethyl ester, t-butyl ester, cholesteryl ester, isopropyl ester and glyceryl ester.

* * * * *

SEQUENCE LISTING (1) GENERAL INFORMATION:

(iii) NUMBER OF SEQUENCES:22

(2) INFORMATION FOR SEQ ID NO:1:

(i) SEQUENCE CHARACTERISTICS:
      (A) LENGTH:4
      (B) TYPE:amino acid
      (C) STRANDEDNESS:single
      (D) TOPOLOGY:linear (xi) SEQUENCE DESCRIPTION: SEQ ID NO:1:

Cys Ala Ala Xaa
        4

(2) INFORMATION FOR SEQ ID NO:2:

(i) SEQUENCE CHARACTERISTICS:
      (A) LENGTH:4
      (B) TYPE:amino acid
      (C) STRANDEDNESS:single
      (D) TOPOLOGY:linear (xi) SEQUENCE DESCRIPTION: SEQ ID NO:2:

Xaa Xaa Xaa Xaa
        4

(2) INFORMATION FOR SEQ ID NO:3:

(i) SEQUENCE CHARACTERISTICS:
      (A) LENGTH:4
      (B) TYPE:amino acid

```
        (C) STRANDEDNESS:single
        (D) TOPOLOGY:linear (xi) SEQUENCE DESCRIPTION: SEQ ID NO:3:

Xaa Xaa Xaa Xaa
            4

(2) INFORMATION FOR SEQ ID NO:4:

(i) SEQUENCE CHARACTERISTICS:
        (A) LENGTH:4
        (B) TYPE:amino acid
        (C) STRANDEDNESS:single
        (D) TOPOLOGY:linear (xi) SEQUENCE DESCRIPTION: SEQ ID NO:4:

Xaa Xaa Xaa Xaa
            4

(2) INFORMATION FOR SEQ ID NO:5:

(i) SEQUENCE CHARACTERISTICS:
        (A) LENGTH:4
        (B) TYPE:amino acid
        (C) STRANDEDNESS:single
        (D) TOPOLOGY:linear (xi) SEQUENCE DESCRIPTION: SEQ ID NO:5:

Cys Val Xaa Met
            4

(2) INFORMATION FOR SEQ ID NO:6:

(i) SEQUENCE CHARACTERISTICS:
        (A) LENGTH:4
        (B) TYPE:amino acid
        (C) STRANDEDNESS:single
        (D) TOPOLOGY:linear (xi) SEQUENCE DESCRIPTION: SEQ ID NO:6:

Cys Val Xaa Met
            4

(2) INFORMATION FOR SEQ ID NO:7:

(i) SEQUENCE CHARACTERISTICS:
        (A) LENGTH:4
        (B) TYPE:amino acid
        (C) STRANDEDNESS:single
        (D) TOPOLOGY:linear (xi) SEQUENCE DESCRIPTION: SEQ ID NO:7:

Cys Val Xaa Met
            4

(2) INFORMATION FOR SEQ ID NO:8:

(i) SEQUENCE CHARACTERISTICS:
        (A) LENGTH:4
        (B) TYPE:amino acid
        (C) STRANDEDNESS:single
        (D) TOPOLOGY:linear (xi) SEQUENCE DESCRIPTION: SEQ ID NO:8:

Cys Val Xaa Met
            4

(2) INFORMATION FOR SEQ ID NO:9:
```

```
        (i) SEQUENCE CHARACTERISTICS:
             (A) LENGTH:4
             (B) TYPE:amino acid
             (C) STRANDEDNESS:single
             (D) TOPOLOGY:linear (xi) SEQUENCE DESCRIPTION: SEQ ID NO:9:

Cys Xaa Xaa Met
          4

(2) INFORMATION FOR SEQ ID NO:10:

(i) SEQUENCE CHARACTERISTICS:
             (A) LENGTH:4
             (B) TYPE:amino acid
             (C) STRANDEDNESS:single
             (D) TOPOLOGY:linear (xi) SEQUENCE DESCRIPTION: SEQ ID NO:10:

Cys Xaa Xaa Met
          4

(2) INFORMATION FOR SEQ ID NO:11:

(i) SEQUENCE CHARACTERISTICS:
             (A) LENGTH:4
             (B) TYPE:amino acid
             (C) STRANDEDNESS:single
             (D) TOPOLOGY:linear (xi) SEQUENCE DESCRIPTION: SEQ ID NO:11:

Cys Xaa Xaa Met
          4

(2) INFORMATION FOR SEQ ID NO:12:

(i) SEQUENCE CHARACTERISTICS:
             (A) LENGTH:4
             (B) TYPE:amino acid
             (C) STRANDEDNESS:single
             (D) TOPOLOGY:linear (xi) SEQUENCE DESCRIPTION: SEQ ID NO:12:

Cys Xaa Phe Met
          4

(2) INFORMATION FOR SEQ ID NO:13:

(i) SEQUENCE CHARACTERISTICS:
             (A) LENGTH:4
             (B) TYPE:amino acid
             (C) STRANDEDNESS:single
             (D) TOPOLOGY:linear (xi) SEQUENCE DESCRIPTION: SEQ ID NO:13:

Cys Xaa Phe Met
          4

(2) INFORMATION FOR SEQ ID NO:14:

(i) SEQUENCE CHARACTERISTICS:
             (A) LENGTH:4
             (B) TYPE:amino acid
             (C) STRANDEDNESS:single
             (D) TOPOLOGY:linear (xi) SEQUENCE DESCRIPTION: SEQ ID NO:14:

Cys Xaa Phe Met
```

4

(2) INFORMATION FOR SEQ ID NO:15:

(i) SEQUENCE CHARACTERISTICS:
        (A) LENGTH:4
        (B) TYPE:amino acid
        (C) STRANDEDNESS:single
        (D) TOPOLOGY:linear (xi) SEQUENCE DESCRIPTION: SEQ ID NO:15:

Cys Xaa Xaa Met
          4

(2) INFORMATION FOR SEQ ID NO:16:

(i) SEQUENCE CHARACTERISTICS:
        (A) LENGTH:4
        (B) TYPE:amino acid
        (C) STRANDEDNESS:single
        (D) TOPOLOGY:linear (xi) SEQUENCE DESCRIPTION: SEQ ID NO:16:

Cys Val Phe Met
          4

(2) INFORMATION FOR SEQ ID NO:17:

(i) SEQUENCE CHARACTERISTICS:
        (A) LENGTH:4
        (B) TYPE:amino acid
        (C) STRANDEDNESS:single
        (D) TOPOLOGY:linear (xi) SEQUENCE DESCRIPTION: SEQ ID NO:17:

Cys Ala Ala Leu
          4

(2) INFORMATION FOR SEQ ID NO:18:

(i) SEQUENCE CHARACTERISTICS:
        (A) LENGTH:4
        (B) TYPE:amino acid
        (C) STRANDEDNESS:single
        (D) TOPOLOGY:linear (xi) SEQUENCE DESCRIPTION: SEQ ID NO:18:

Cys Val Leu Ser
          4

(2) INFORMATION FOR SEQ ID NO:19:

(i) SEQUENCE CHARACTERISTICS:
        (A) LENGTH:4
        (B) TYPE:amino acid
        (C) STRANDEDNESS:single
        (D) TOPOLOGY:linear (xi) SEQUENCE DESCRIPTION: SEQ ID NO:19:

Cys Val Ile Met
          4

(2) INFORMATION FOR SEQ ID NO:20:

(i) SEQUENCE CHARACTERISTICS:
        (A) LENGTH:4
        (B) TYPE:amino acid
        (C) STRANDEDNESS:single
        (D) TOPOLOGY:linear

```
        (xi) SEQUENCE DESCRIPTION: SEQ ID NO:20:

Xaa Xaa Xaa Xaa
                4

(2) INFORMATION FOR SEQ ID NO:21:

(i) SEQUENCE CHARACTERISTICS:
           (A) LENGTH:4
           (B) TYPE:amino acid
           (C) STRANDEDNESS:single
           (D) TOPOLOGY:linear (xi) SEQUENCE DESCRIPTION: SEQ ID NO:21:

Xaa Xaa Xaa Xaa
                4

(2) INFORMATION FOR SEQ ID NO:22:

(i) SEQUENCE CHARACTERISTICS:
           (A) LENGTH:4
           (B) TYPE:amino acid
           (C) STRANDEDNESS:single
           (D) TOPOLOGY:linear (xi) SEQUENCE DESCRIPTION: SEQ ID NO:22:

Cys Val Leu Leu
```